United States Patent [19]

Campbell, Jr. et al.

[11] Patent Number: 5,608,075

[45] Date of Patent: Mar. 4, 1997

[54] POLYMORPHS OF LOSARTAN AND THE PROCESS FOR THE PREPARATION OF FORM II OF LOSARTAN

[75] Inventors: Gordon C. Campbell, Jr., Wilmington; Anil M. Dwivedi, Newark, both of Del.; Dorothy A. Levorse, South Amboy; James A. McCauley, Bellemeade, both of N.J.; Krishnaswamy S. Raghavan, Wilmington, Del.

[73] Assignees: Merck & Co., Inc., Rahway, N.J.; E. I. Du Pont de Nemours & Company; The DuPont Merck Pharmaceutical Company, both of Wilmington, Del.

[21] Appl. No.: 371,937

[22] Filed: Jan. 12, 1995

Related U.S. Application Data

[63] Continuation of Ser. No. 173,440, Dec. 23, 1993, abandoned.

[51] Int. Cl.$^6$ .................................................. C07D 257/04
[52] U.S. Cl. .................................................. 548/252
[58] Field of Search .................................................. 548/252

[56] References Cited

U.S. PATENT DOCUMENTS

| | | | |
|---|---|---|---|
| 5,130,439 | 7/1992 | Lo et al. | 548/110 |
| 5,138,069 | 8/1992 | Carini et al. | 548/253 |
| 5,206,374 | 4/1993 | Lo et al. | 548/110 |
| 5,310,928 | 5/1994 | Young et al. | |

OTHER PUBLICATIONS

K. S. Raghavan et al., "A Spectroscpic Investigation of Losartan Polymorphs", Pharmaceutical Research, vol. 10, No. 6, pp. 900–904 (1993).

Lei–Shu Wu, et al., "Thermal Analysis and Solution Calorimetry Studies on Losartan Polymorphs", Pharmaceutical Research, vol. 10, No. 12 pp. 1793–1795 (1993).

*Primary Examiner*—David B. Springer
*Attorney, Agent, or Firm*—Valerie J. Camara; Mark R. Daniel

[57] ABSTRACT

Polymorphic forms of Losartan (Formula I)

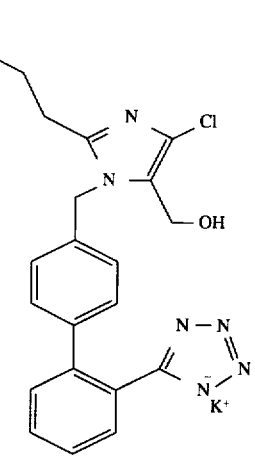

FORMULA I and a process for the preparation of Form II of Losartan. Losartan is known to be useful in the treatment of hypertension.

11 Claims, 8 Drawing Sheets

POLYMORPHS OF LOSARTAN AND THE PROCESS FOR THE PREPARATION OF FORM II OF LOSARTAN

This is a continuation of application Ser. No. 08/173,440 filed on Dec. 23, 1993, now abandoned.

BACKGROUND OF THE INVENTION

This invention relates to the polymorphic forms of Losartan and the process for morphologically homogenous Losartan. Losartan is well known as 2-butyl-4-chloro-1-[(2'-tetrazol-5-yl)-biphenyl-4-yl]methyl]-5-(hydroxymethyl)imidazole potassium salt has been shown to be useful in the treatment of hypertension.

The compounds of this invention, the polymorphic forms of Losartan, are known to inhibit the action of the octapeptide hormone angiotensin II (AII) and are useful therefore in alleviating angiotensin induced hypertension. The enzyme renin acts on a blood plasma α2-globulin, angiotensinogen, to produce angiotensin I, which is then converted by angiotensin converting-enzyme to AII. The latter substance is a powerful vasopressor agent which has been implicated as a causitive agent for producing high blood pressure in various mammalian species, such as the rat, dog, and man. The compounds of this invention inhibit the action of AII at its receptors on target cells and thus prevent the increase in blood pressure produced by this hormone-receptor interaction. By administering a compound of this invention to a species of mammal with atherosclerosis and/or high cholesterol and/or hypertension due to AII, the blood pressure is reduced. The compounds of this invention are also useful for the treatment of high cholesterol by reducing the total cholesterol. Administration of a compound of this invention with a diuretic such as furosemide or hydrochlorothiazide, either as a stepwise combined therapy (diuretic first) or as a physical mixture, enhances the antihypertensive effect of the compound, while also treating atherosclerosis and reducing cholesterol levels. Administration of a compound of this invention with a non-steroidal anti-inflammatory drug (NSAID) can prevent renal failure which sometimes results from administration of a NSAID.

K. Matsumura, et al., in U.S. Pat. No. 4,207,324 issued Jun. 10, 1980, discloses 1,2-disubstituted-4-haloimidazole-5-acetic acid derivatives of the formula:

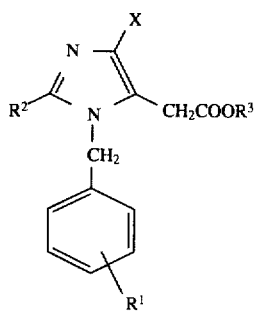

Wherein $R^1$ is hydrogen, nitro or amino; $R^2$ is phenyl, furyl or thienyl optionally substituted by halogen, lower alkyl, lower alkoxy or di-lower alkylamino; $R^3$ is hydrogen or lower alkyl and X is halogen; and their physiologically acceptable salts. These compounds have diuretic and hypotensive actions.

Furukawa, et al., in U.S. Pat. No. 4,355,040 issued Oct. 19, 1982, discloses hypotensive imidazole-5-acetic acid derivatives having the formula:

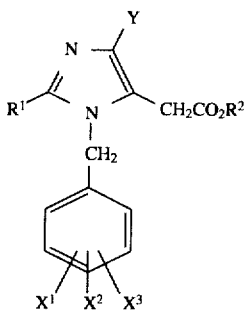

Wherein $R^1$ is lower alkyl, cycloalkyl, or phenyl optionally substituted; $X^1$, $X^2$, and $X^3$ are each hydrogen, halogen, nitro, amino, lower alkyl, lower alkoxy, benzyloxy, or hydroxy; Y is halogen and $R^2$ is hydrogen or lower alkyl; and salts thereof.

Furukawa, et al., in U.S. Pat. No. 4,340,598, issued Jul. 20, 1982, discloses hypotensive imidazole derivatives of the formula:

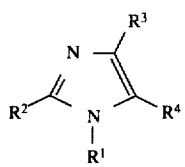

Wherein $R^1$ is lower alkyl or, phenyl $C_{1-2}$ alkyl optionally substituted with halogen or nitro; $R^2$ is lower alkyl, cycloalkyl or phenyl optionally substituted; one of $R^3$ and $R^4$ is —$(CH_2)_nCOR^5$ where $R^5$ is amino, lower alkoxyl or hydroxyl and n is 0, 1, 2 and the other of $R^3$ and $R^4$ is hydrogen or halogen; provided that $R^1$ is lower alkyl or phenethyl when $R^3$ is hydrogen, n=1 and $R^5$ is lower alkoxyl or hydroxyl; and salts thereof.

Furukawa, et al., in European Patent Application 103,647 discloses 4-chloro-2-phenylimidazole-5-acetic acid derivatives useful for treating edema and hypertension of the formula:

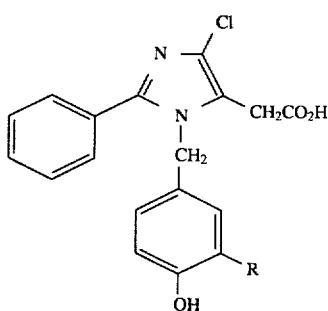

Where R represents lower alkyl and salts thereof.

The metabolism and disposition of hypotensive agent 4-chloro-1-(4-methoxy-3-methylbenzyl)-2-phenyl-imidazole-5-acetic acid is disclosed by H. Torii in *Takeda Kenkyushoho*, 41, No 3/4, 180–191 (1982).

Frazee, et al., in European Patent Application 125,033-A discloses 1-phenyl(alkyl)-2-(alkyl)-thioimidazole derivatives which are inhibitors of dopamine-β-hydroxylase and are useful as antihypertensives, diuretics and cardiotonics.

European Patent Application 146,228 filed Oct. 16, 1984, by S. S. L. Parhi discloses a process for the preparation of 1-substituted-5-hydroxymethyl-2-mercaptoimidazoles.

A number of references disclose 1-benzyl-imidazoles such as U.S. Pat. Nos. 4,448,781 to Cross and Dickinson (issued May 15, 1984); 4,226,878 to Ilzuka, et al. (issued Oct. 7, 1980); 3,772,315 to Regel, et al. (issued Nov. 13, 1973); 4,379,927 to Vorbruggen, et al. (issued Apr. 12, 1983); amongst others.

Pals, et al., Circulation Research, 29, 673 (1971) describe the introduction of a sarcosine residue in position 1 and alanine in position 8 of the endogenous vasoconstrictor hormone AII to yield an (octa)peptide that blocks the effects of AII on the blood pressure of pithed rats. This analog, [$Sar^1$, $Ala^8$] AII, initially called "P-113" and subsequently "Saralasin," was found to be one of the most potent competitive antagonists of the actions of AII, although, like most of the so-called peptide-AII-antagonists, it also possesses agonistic actions of its own. Saralasin has been demonstrated to lower arterial pressure in mammals and man when the (elevated) pressure is dependent on circulating AII (Pals al., Circulation Research, 29, 673 (1971); Streeten and Anderson, Handbook of Hypertension, Vol. 5, Clinical Pharmacology of Antihypertensive Drugs, A. E. Doyle (Editor), Elsevier Science Publishers B. V., p. 246 (1984)). However, due to its agonistic character, saralasin generally elicits pressor effects when the pressure is not sustained by AII. Being a peptide, the pharmacological effects to saralasin are relatively short-lasting and are only manifest after parenteral administration, oral doses being ineffective. Although the therapeutic uses of peptide AII-blockers, like saralasin, are severely limited due to their oral ineffectiveness and short duration of action, their major utility is as a pharmaceutical standard.

Currently there are several AII antagonists in development. Among these development candidates, is Losartan which is disclosed in a U.S. Pat. No. 5,138,069 issued to DuPont on Aug. 11, 1992. Losartan has been demonstrated to be an orally active AII antagonists, selective for the $AT_1$ receptor subtype.

Some known non-peptide antihypertensive agents act by inhibiting an enzyme, called angiotensin converting enzyme (ACE), which is responsible for conversion of angiotensin I to AII. Such agents are thus referred to as ACE inhibitors, or converting enzyme inhibitors (CEI's). Captopril and enalapril are commercially available CEI's. Based on experimental and clinical evidence, about 40% of hypertensive patients are non-responsive to treatment with CEI's. But when a diuretic such as furosemide or hydrochlorothiazide is given together with a CEI, the blood pressure of the majority of hypertensive patients is effectively normalized. Diuretic treatment converts the non-renin dependent state in regulating blood pressure to a renin-dependent state. Although the imidazoles of this invention act by a different mechanism, i.e., by blocking the AII receptor rather than by inhibiting the angiotensin converting enzyme, both mechanisms involve interference with the renin-angiotensin cascade. A combination of the CEI enalapril maleate and the diuretic hydrochlorothiazide is commercially available under the trademark Vaseretic® from Merck & Co. Publications which relate to the use of diuretics with CEI's to treat hypertension, in either a diuretic-first, stepwise approach or in physical combination, include Keeton, T. K. and Campbell, W. B., Pharmacol. Rev., 31:81 (1981) and Weinberger, M. H., Medical Clinics N. America, 71:979 (1987). Diuretics have also been administered in combination with saralasin to enhance the antihypertensive effect.

Non-steroidal anti-inflammatory drugs (NSAID's) have been reported to induce renal failure in patients with renal under perfusion and high plasma level of AII. (Dunn, M. J., Hospital Practice, 19:99, 1984). Administration of an AII blocking compound of this invention in combination with an NSAID (either stepwise or in physical combination) can prevent such renal failure. Saralasin has been shown to inhibit the renal vasoconstrictor effect of indomethacin and meclofenamate in dogs (Satoh, et al., Circ. Res. 36/37 (Suppl. I):I-89, 1975; Blasingham, et al., Am J. Physiol. 239:(F360, 1980). The CEI captopril has been demonstrated to reverse the renal vasoconstrictor effect of indomethacin in dogs with non-hypotensive hemorrhage. (Wong, et al., J. Pharmacol. Exp. Ther. 219:104, 1980).

Infrared and Raman spectroscopies have been widely used to elucidate molecular structures, crystallinity and polymorphism. The low-frequency Raman modes are particularly useful in distinguishing different molecular packings in crystals. (J. C. Decius and R. M. Hexter. Molecular Vibrations in Crystals, McGraw-Hill, New York, 1977). Solid -state $^{13}C$ NMR spectroscopy is also used in the characterization of pharmaceutical compounds. H. Y. Aboul-Enein. Applications of solid-state Nuclear Magnetic resonance spectroscopy to pharmaceutical research', Spectroscopy 5(3):32 (1990). $^{13}C$ spectra acquired using a combination of cross polarization (CP) as described by A. Pines et al. J. Chem Phys. 59:569–590 (1973) for sensitivity enhancement with magic-angle spinning (MAS) as described by E. R. Andrews et al. in Nature (Lond.) 183:1802–1803 (1959) and high-power proton decoupling for resolution enhancement have been shown to provide relevant structural and dynamic information.(S. R. Byrn et al., Trans. Am. Crystallogr. Assoc. 24:41–54 (1989)).

Figure 1A:
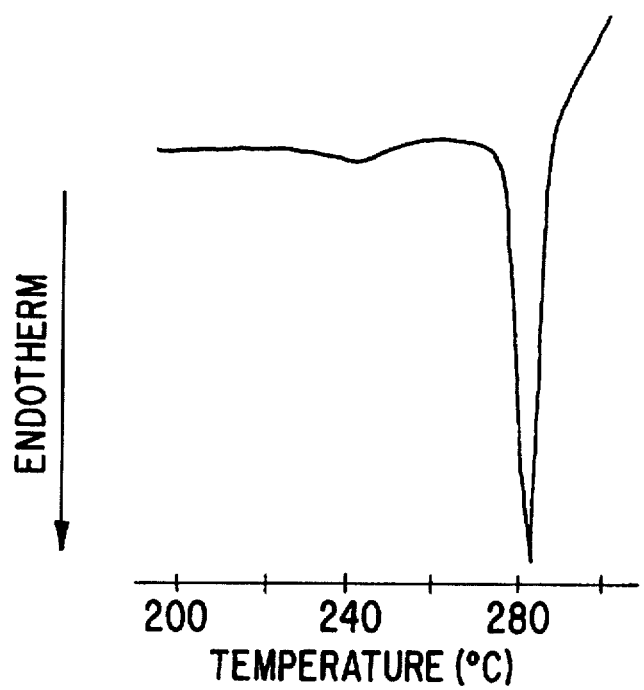
FIG. 1.

DSC thermograms of Losartan (A) before heating and (B) after heat treatment at 255° C. The heating rate was 10° C. per minute. The material before heat treatment is identified as Form I and the material which has been heat treated is identified as Form II.

FIG. 2.

X-ray powder diffraction pattern of Losartan polymorphs: (A) Form I and (B) Form II.

FIG. 3.

5 FTIR spectra of Losartan polymorphs from 1150 $cm^{-1}$ to 600 $cm^{-1}$: (A) Form I and (B) Form II.

FIG. 4.

FTIR spectra of Losartan polymorphs from 1800 $cm^{-1}$ to 1150 $cm^{-1}$: (A) Form I and (B) Form II.

FIG. 5.

Raman spectra of Losartan polymorphs from 1100 $cm^{-1}$ to 600 $cm^{-1}$: (A) Form I and (B) Form II.

FIG. 6.

Raman spectra of Losartan polymorphs from 180 $cm^{-1}$ to 400 $cm^{-1}$: (A) Form I and (B) Form II.

FIG. 7.

Solid-state 13CP/MAS NMR spectra [upfield region] of Losartan polymorphs: (A) Form I and (B) Form II.

FIG. 8.

Solid-state 13CP/MAS NMR spectra [downfield region] of Losartan polymorphs: (A) Form I and (B) Form II.

DETAILED DESCRIPTION OF THE INVENTION

This invention relates to the two polymorphic forms of Losartan, 'Forms I' and 'Form II', and the process for the preparation of Form II of Losartan. Losartan is well known as 2-butyl-4-chloro-1-[(2'-tetrazol-5-yl)-biphenyl-4-yl]methyl]-5-(hydroxy-methyl)imidazole potassium salt (Formula I) has been shown to be useful in the treatment of hypertension as an $AT_1$ selective Angiotensin II antagonist.

FORMULA I

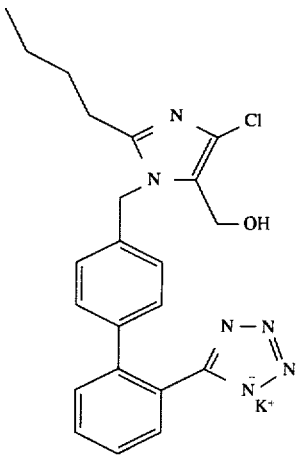

SYNTHESIS

Losartan may be prepared using the reactions and techniques described in U.S. Pat. No. 5,138,069 and WO 93/10106 or one of its three U.S. counterparts, U.S. Pat. No. 5,130,439 issued Jul. 14, 1992, U.S. Pat No. 5,206,374 issued Apr. 27, 1993, and U.S. Ser. No. 07/911,813 filed Jul. 10, 1992.

The following examples further illustrate the preparation of Losartan, the compound of Formula I, the identification of the polymorphic forms of Losartan referred to as 'Form I' and 'Form II' and the process for the preparation of morphologically homogenous Losartan and, as such, are not be considered or construed as limiting the invention recited in the appended claims.

EXAMPLE 1

2-n-butyl-4-chloro-5-hydroxymethyl-1-[(2-(1H-tetrazol-5-yl)biphenyl-4-yl)methyl]imidazole [DuP-7531]

Step A: Preparation 4'- methylbiphenyl-2-carboxylic acid

Methyl 4'-methylbiphenyl-2-carboxylate (10.0 g, 44.2 mmol, 1 eq), 0.5N KOH in methanol (265.5 mL, 133 mmol, 3 eq), and water (50 mL) were mixed and refluxed under $N_2$. After 5 hours, the solvent was removed in vacuo and water (200 mL) and ethyl acetate (200 mL) added. The aqueous layer was acidified with concentrated hydrochloric acid to a pH of 3 and the layers were separated. The aqueous phase was extracted with ethyl acetate (2×200 mL), the organic layers collected, dried (MgSO$_4$) and the solvent removed in vacuo to yield 8.71 g of a white solid; m.p. 140.0°–145.0°. NMR (200 MHz, DMSO-d$_6$)δ7.72 (d, 1H, J=7 Hz); 7.56 (t, 1H, J=7 Hz); 7.45 (d, 1H, J=7 Hz); 7.40 (t, 1H, J=7 Hz); 7.25 (s, 4H); 2.36 (s, 3H). Anal Calcd. for $C_{14}H_{12}O_2$; C, 79.23; H, 5.70. Found: C, 79.22; H, 5.47.

Step B: Preparation of 4'-Methyl-2-cyanobiphenyl

4'-Methylbiphenyl-2-carboxylic acid (8.71 g, 41 mmol, 1 eq) and thionyl chloride (30.0 mL, 411 mmol, 10 eq) were mixed and refluxed for 2 hours. The excess thionyl chloride was removed in vacuo and the residue was taken up in toluene. The toluene was removed by rotary evaporation and this toluene evaporation procedure was repeated to ensure that all of the thionyl chloride was removed. The crude acid chloride was then added slowly to cold (0° C.) concentrated NH$_4$OH (50 mL) so that the temperature was kept below 15°. After 15 minutes of stirring, water (100 mL) was added and solids precipitated. These were collected, washed well with water and dried under high vacuum over $P_2O_5$ in a dessicator overnight to yield 7.45 g of white solid; m.p. 126.0°–128.5°. NMR (200 MHz, DMSO-d$_6$)δ 7.65–7.14 (m, 10H), 2.32 (s, 3H).

Anal Calcd. for $C_{14}H_{13}NO$: C, 79.59; H, 6.20; N, 6.63. Found: C, 79.29; H, 6.09; N, 6.52.

The above product amide (7.45 g, 35 mmol, 1 eq) and thionyl chloride (25.7 mL, 353 mmol, 10 eq) were mixed and refluxed for 3 hours. The thionyl chloride was removed using the same procedure as described above. The residue was washed with a little hexane which partly solubilized the product, but removed the impurity as well to yield 6.64 g of white solid; m.p. 44.00°–47.0°. NMR (200 MHz, DMSO-d$_6$)δ7.95 (d, 1H, J=8 Hz); 7.78 (t, 1H, J=7 Hz); 7.69–7.32 (m, 6H); 2.39 (s, 3H).

Anal Calcd. for $C_{14}H_{11}N$: C, 87.01; H, 5.74. Found: C, 86.44; H, 5.88.

Step C: Preparation of 4'-bromomethyl-2-cyanobiphenyl

A solution of 5.59 g of 4'-methyl-2-cyanobiphenyl, 29 mmol of N-bromosuccinimide, 0.9 mmol of benzoylperoxide and 500 mL of carbon tetrachloride was refluxed for 3 hours. After cooling to room temperature, the resulting suspension was filtered and then concentrated in vacuo to provide the crude 4'-bromomethyl-2-cyanobiphenyl. The product was recrystallized from ether to yield 4.7 g of product; m.p. 114.5°–120.0°. NMR (200 MHz, CDCl$_3$)δ7.8214 7.37 (m, 8H); 4.50 (s, 2H).

Anal. Calcd. for $C_{14}H_{10}BrN$: C, 61.79, H, 3.70; N, 5.15. Found: C, 62.15; H, 3.45; N, 4.98.

Step D: Preparation of 2-n-butyl-4-chloro-1-[2'-cyanobiphenyl-4-yl)methyl]-5-(hydroxymethyl)-imidazole To a suspension of 1.43 g of sodium methoxide in 20 mL of dimethylformamide at 25° was added a solution of 15.3 mmol of 2-butyl-4(5)-chloro-5(4)-hydroxymethyl imidazole (prepared as described in U.S. Pat. No. 4,355,040) in 15 mL of DMF. The resulting mixture was stirred at 25° for 0.25 hours, and then to this mixture 4.6 g, 16.9 mmol of 4'-bromomethyl-2-cyanobiphenyl in 15 mL of DMF. Finally, the reaction mixture was stirred at 40° for 4 hours. After cooling to 25°, the solvent was removed in vacuo. The residue was dissolved in 1:1 hexane/ethyl acetate, and this solution was washed with water and brine, dried over anhydrous sodium sulfate, filtered, and concentrated. The crude product contains two regioisomers, the faster moving one by TLC being the more potent isomer. Flash chromatography in 1:1 hexane/ethyl acetate over silica gel to separate the regioisomeric products yielded 2.53 g of the faster eluting isomer. Recrystallization from acetonitrile yielded 1.57 g of analytically pure product; m.p. 153.5°–155.5°. NMR (200 MHz, CDCl$_3$)δ7.82–7.43 (m, 6); 7.12 (d, 2, J=8 Hz); 5.32 (s, 2); 4.52 (s, 2); 2.62 (t, 2, J=7 Hz); 1.70 (t of t, 2, J=7.7 Hz); 1.39 (t of q, 2, J=7,7 Hz); 0.90 (t, 3, J=7 Hz).

Anal. Calcd. for $C_{22}H_{22}ClN_3O$: C, 69.56; H, 5.84; N, 11.06. Found: C, 69.45; H, 5.89; N, 10.79.

Step E: Preparation of 2-n-butyl-4-chloro-5-hydroxymethyl-1-[(2'-(1H-tetrazol-5-yl)biphenyl-4-yl)methyl]imidazole 2-n-Butyl-4-chloro-1-[(2'-cyanobiphenyl-4-yl)-methyl]-5-(hydroxymethyl)imidazole (11.93 g, 1.0 eq), sodium azide (3 eq), and ammonium chloride (3 eq) were mixed and stirred in DMF (150 mL) in a round bottom connected to a reflux condenser under $N_2$. An oil bath with a temperature controller was then used to heat the reaction at 100° C. for 2 days, after which the temperature was raised to 120° C., for 6 days. The reaction was cooled and 3 more equivalents of ammonium chloride and sodium azide were added. The reaction was again heated for 5 more days at 120° C. The reaction was cooled, the inorganic salts filtered, and the filtrate solvent removed in vacuo. Water (200 mL) and ethyl acetate (200 mL) were added to the residue and the layers were separated. The aqueous layer was extracted with ethyl acetate (2×200 mL), the organic layers were collected, dried (MgSO$_4$) and the solvent removed in vacuo, to yield a dark yellow oil. The product was purified by flash chromatography in 100% ethyl acetate to 100% ethanol over silica gel to yield 5.60 g of a light yellow solid. Recrystallization from acetonitrile yielded 4.36 g of light yellow crystals which still melted broadly. The crystals were taken up in 100 mL of hot acetonitrile. The solid that did not dissolve was filtered off to yield 1.04 g of product as a light yellow solid; m.p. 183.5°–184.5°. Upon cooling, the mother liquor yielded an additional 1.03 g of product as a light yellow solid; m.p. 179.0°–180.0°. NMR (200 MHz, DMSO-d$_6$)δ7.75–7.48 (m, 4H); 7.07 (d, 2H, J=9 Hz); 7.04 (d, 2H, J=9 Hz); 5.24 (s, 2H); 5.24 (bs, 1H); 4.34 (s, 2H); 2.48 (t, 2H, J=7 Hz); 1.48 (t of t, 2H, J=7,7 Hz); 1.27 (t of q, 2H, J=7,7 Hz); 0.81 (t, 3H, J=7 Hz).

Anal. Calcd. for C$_{22}$H$_{23}$ClN$_6$O: C, 62.48; H, 5.48; Cl, 8.38.

Found for the solids which did not dissolve in 100 mL of acetonitrile: C, 62.73; H, 5.50; Cl, 8.26.

Found for the solids obtained from the mother liquor: C, 62.40; H, 5.23; Cl, 8.35.

CAUTION!! The above reaction although uneventful in our hands can be potentially explosive Crystals that sublime and collected in the reflux condenser during the reaction were not analyzed, but potentially could be ammonium azide. Hydrazoic acid, which is shock sensitive, could also be potentially produced during the reaction and workup. Extreme care should be taken!

EXAMPLE 2

2-n- Butyl-4-chloro-1-[(2'-(2-triphenylmethyl-2H-tetrazol-5-yl)-1,1'-biphenyl-4-yl )methyl]-1H-imidazole-5-methanol Step A: 2-(2'-Triphenylmethyl-2'H-tetrazol-5'-yl)phenylboronic acid
Alternative 1

To a 22 L flask under nitrogen purge was charged 8.25 L acetone, followed by 1.1 kg 5-phenyltetrazole. Triethylamine (800 g) was added in such a rate that the temperature was maintained below 35° C. with some cooling. Solid trityl chloride was charged to this light suspension in five 440 g portions. The temperature was maintained below 35° C. An additional 1.38 L acetone was added to the reaction which was then maintained at 25° to 30° C. with stirring for 2 hours. Water (2.2 L) was added and the mixture was chilled to 15° to 20° C. The solid was collected by filtration; the filter cake was rinsed with 1.65 L 50% acetone-water followed by excess amount of water. The wet cake was re-slurried in 8 L acetone and 8 L of water was added slowly. The suspension was stirred for 1 hour then filtered. The filter cake was rinsed with 3 to 5 L of water. The white solid was dried in a vacuum oven at 40°–45° C. to a constant weight of 3.0 kg, mp 158°–160° C.

To a dry 12 L flask under nitrogen purge was charged 3.19 L of dry tetrahydrofuran (THF). With agitation, 398 g of 5-phenyl-2-trityl-tetrazole prepared above was charged. The system was evacuated and released to nitrogen three times and then cooled to –20° C. A solution of butyl lithium in heptane (1.6M, 477 g) was then added to the reaction mixture while maintaining the temperature at –15° C. to –20° C. The resultant deep red solution was stirred at –5° C. for 1 hour during which time the lithium salt crystallized out. The solid suspension was cooled to –25° C. again and 333 g triisopropylborate was charged at a temperature range of –20° to –25° C. After the addition, the mixture was allowed to warm to 20° C. without heating. About 2.5 L of solvent was removed by vacuum distillation. The pot temperature was kept below 40° C. To the mixture was then added 2.66 L of 3% acetic acid in water and the resultant suspension was stirred for 1 hour. The white solid was collected by filtration. The solid cake was rinsed with 1.5 L of 20% tetrahydrofuran in water, followed by 3 L of water. The solid was dried under vacuum at room temperature to a constant weight of 502.3 g, mp 142°–146° C. (dec.).
Alternative 2

A preferred alternative procedure for preparing the title compound is by means of the following procedure.

5-Phenyltetrazole (14.6 g, 100 mmol) was suspended in dry THF (120 ml) under nitrogen and triethylamine (14.8 ml, 105 mmol) was added while maintaining the temperature at 15° to 20° C. Triphenylchloromethane (29.3 g, 105 mmol) in dry THF (60 ml) was then added slowly to the mixture at ≦25° C. After the addition was complete the mixture was warmed to 35° C. for 1 hour and then cooled at 0° C. for 1 hour. The precipitated triethylammonium chloride was filtered and the filtrate was degassed via vacuum/nitrogen purges (3×). The degassed solution was cooled to –20° C. and butyllithium (1.6M in hexanes) was added until a pink color persisted for 2 minutes. The pink color indicated that the solution was completely dry. More butyllithium (65.6 ml, 105 mmol) was charged at ≦–15° C. The deep red hetero-geneous mixture was aged at –20° to –15° C. for 1 hour and triisopropylborate (30.6 ml, 130 mmol) was added while maintaining the temperature at ≦–15° C.

The deep red solution was aged at –15° C. for 30 minutes and then warmed to 10° C. over 1 hour. The mixture volume was reduced by ~200 ml in vacuo at ≦15° C. at which time <5% of hexanes (vs THF) remained. The residue was diluted with THF to a total volume of 160 ml and isopropanol (60 ml) was added. The solution was cooled to 0° C. and saturated aqueous ammonium chloride (40 ml, 200 mmol) was charged within 15 minutes. The mixture was aged at 20 to 25° C. for 30 minutes and water (100 ml) was added over 30 to 45 minutes. After aging the mixture for 1 hour, the crystallized product was collected by filtration and washed with cold 80% aqueous isopropanol. The filter cake was air dried on the filter to give 69.7 g (86% yield, corrected for 82% purity) of product as the THF mono-solvate.
Step B: 2-n-butyl-4-chloro-5-hydroxymethyl-1-p-bromobenzyl-1H-imidazole A suspension of 2-n-butyl-4-chloro-1H-imdazole-5carboxyaldehyde (146.9 g, 0.78 mol) and p-bromobenzyl bromide (195 g, 0.78 mol) in dimethylacetamide (1.0 L) was cooled to 0° C. and potassium carbonate (1.38 g, 1.0 mol) was added. The mixture was aged for three hours at 0° C. and then at 20° to 25° C. or two to four hours. The mixture was diluted with dimethylacetamide (0.15 L) and then filtered. The filter cake was washed with dimethylacetamide (50 ml). The combined filtrates were diluted with methanol (0.66 L) and cooled to 0° C. Sodium borohydride (37.8 g, 1.0 mol) was added as a solid and the mixture was aged with stirring at 20° to 25° C. for two hours. Water (1.56 L) was added slowly to crystallize the product. The filter cake was washed carefully with water (1.56 L) and dried in vacuo at 60° C. The yield was 255 g (91%, corrected for 99.5% purity).

Step C: 2-n-butyl-4-chloro-1-[(2'-(2-triphenylmethyl-2H-tetrazol-5-yl)-1,1'-biphenyl-4-yl)methyl]-1H-imidazole-5-methanol All operations described for this example were performed under an atmosphere of nitrogen.

Catalyst preparation

To a mixture of palladium chloride (10.6 mg) and triphenylphosphine (31.5 mg) was added anhydrous toluene (4 ml). The heterogeneous solution was degassed by vacuum/nitrogen purges (3×) and then heated to 60° C. for 30 minutes. Triisopropylphosphite (30.0 microliters) was added and the mixture was further heated at 60° C. until a homogeneous solution was obtained (1 to 2 hours).

Coupling 2-(2'-triphenylmethyl-2'H-tetrazol-5'-yl)phenylboronic acid of Example 2, Step A (1.3 g) was suspended in toluene (4 ml) and water (100 microliters) was added. The heterogeneous mixture was stirred at room temperature for 30 minutes and potassium carbonate (0.7 g) was then charged followed by the titled product of Example 3, Step B (0.7 g). The mixture was degassed via vacuum/nitrogen purges (3×) and the above catalyst solution was added. The temperature of the mixture was raised 80° to 85° C. and kept at this temperature for 2 hours. After the mixture was cooled to 40° C., water (5 ml) was added. The aqueous layer was removed and the organic phase was concentrated in vacuo at ≦30° C. to a volume of ~3 ml. Methyl i-butyl ketone (MIBK) (8 ml) was added and the mixture was again reduced to ~3 ml. The mixture was diluted with MIBK (4 ml) and water (36 microliters), heated to 60° C. and then cooled and aged first at 0° C. for 30 minutes followed by aging at −10° C. with stirring for 2 hours. The crystallized product was collected by filtration as a mono-MIBK solvate (1.44 g, 94% yield). The crude product was dissolved in MIBK (2.1 ml) at 80° C., the solution was filtered hot at 80° C. and water (33.8 microliters) was added. The solution was cooled slowly to 0° C. over 1 hour and aged at 0° C. for 30 minutes followed by aging at −10° C. with stirring for 2 hours. After filtration 1.38 g of the mono-MIBK solvated product was recovered (90% yield).

EXAMPLE 3

2-n-Butyl-4-chloro-1-[(2'-(2-triphenylmethyl-2H-tetrazol-5-yl)-1,1'-biphenyl-4-yl)methyl]-1H-imidazole-5-methanol All operations described for this example were performed under an atmosphere of nitrogen.

Step A: Catalyst Preparation

The following two procedures can be used with similar results.

Alternative Procedure 1

To a mixture of palladium chloride (354 mg) and triphenylphosphine (2.1 g) was added anhydrous tetrahydrofuran (THF) (75 ml). The heterogeneous solution was degassed by vacuum/nitrogen purges (3×) and then refluxed for 4 hours.

Most of the palladium chloride changed over to bis(triphenylphosphine)palladium chloride during the reflux. Some insoluble black solids were still observed at this point.

The heterogeneous THF solution containing the phosphinated palladium chloride was cooled to room temperature and diethylzinc (4.0 ml, 1M in hexanes) was added. Except for a small amount of black solids, the solution essentially became homogeneous after stirring for 30 minutes. This activated catalyst solution was used in the coupling step described below.

Alternative Procedure 2

To a mixture of palladium chloride (354 mg) and triphenylphosphine (2.1 g) was added anhydrous THF (75 ml). The heterogeneous solution was degassed by vacuum/nitrogen purges (3×) and then triisopropylphosphite (0.99 ml) was added. The mixture was maintained at room temperature until all the palladium chloride was dissolved and a homogeneous solution was obtained (0.5 to 1 hour).

Step B: Benzyltrimethylammonium Carbonate Preparation

To a benzyltrimethylammonium hydroxide solution (42 g) was added ammonium carbonate (5.0 g) and the reaction was aged with stirring until all of the ammonium carbonate dissolved (~30 minutes). The methanol solvent was removed in vacuo and further displaced with THF (3×10 ml). The residual carbonate was dissolved in THF (90 ml).

Step C: Coupling Step

To the carbonate solution prepared in Example 4, Step B was charged the titled product of Example 2 (24.0 g) and the titled product of Example 2, Step B (14.2 g). The mixture was degassed by vacuum/nitrogen purges (5X), followed by the addition of the catalyst solution prepared as recited in Example 3, Step A (procedure 1 or 2). The reaction mixture was heated to reflux, aged until completion (8 to 10 hours), cooled to room temperature and filtered through a pad Celite. The Celite was further washed with THF (3×10 ml). The yield was 89 wt %.

EXAMPLE 4

2-n-Butyl-4-chloro-1-[(2'-(tetrazol-5-yl)-1,1'-biphenyl-4-yl)methyl]-1H-imidazole-5-methanol potassium salt 2-n-butyl-4-chloro-1-[(2'-2-triphenylmethyl-2H-tetrazol-5-yl)-1,1'-biphenyl-4-yl)methyl]-1H-imidazole-5-methanol, obtained from Example 2 or 3, (5.0 g, 6.54 mmol) was dissolved in THF (60 ml). 4N Sulfuric acid (38 ml, 152 mmol) was added with stirring at 25° to 30° C. The solution was aged overnight at 20° to 25° C. and isopropyl acetate (60 ml) was then added. The layers were separated and the organic phase was back-extracted with 4N sulfuric acid (19 ml). The aqueous layers were combined and the organic solvents (THF and isopropyl actate) were removed in vacuo. The remaining aqueous solution was diluted with THF (10% of THF by volume) and passed through a pad of Ecosorb S 402 (5.0 g). The pad was rinsed with 10% THF in 4N sulfuric acid. The filtrate was then passed through a column of SP-207 (60 ml) and the column was washed with water (180 ml) followed with 1M $K_2HPO_4$ (180 ml). The pH of the eluent was monitored to ensure complete potassium salt formation. Further washing with water (180 ml) removed the sulfate and excess phosphate. The potassium salt product was eluted with 20% aqueous THF. Concentration of the aqueous solution and dilution with isopropanol gave crystalline product. Alternatively, the product was isolated by spray drying. The yield was 2.56 g (85%).

EXAMPLE 5

1-Bromo-4-(2'-n-butyl-4'-chloro-5'-hydroxymethylimidazole-1'H-1'-yl)methylbenzene Step A: Alkylation To 200 mL of dimethyl acetamide under a nitrogen atmosphere in a 1-liter 3-necked flask fitted with a mechanical stirrer and thermocouple is charged 30.8 g (0.163 mol) of 2-n-butyl-4-chloro-5-formyl-1H-imidazole and 43.7 g (0.16 mol) of 4-bromobenzyl bromide. The solution is cooled to −5° C. followed by portionwise addition of 27.1 g (0.19 mol) of powdered potassium carbonate over 10 min with rapid stirring while keeping the reaction temperature between −5°—0° C. The slurry is stirred at −5° C. for 2 h and room temperature for 2 h or until the alkylation is complete.

Step B: Filtration

The slurry is filtered and the cake is washed with an anhydrous mixture of dimethyl acetamide (30 mL) and methanol (130 mL). The filtrate is used directly in the next step.

Step C: Reduction

Under a nitrogen atmosphere, 1.85 g (48 mmol) of powdered sodium borohydride is added portionwise over 0.5 h to the filtrate at −15° C. in a 5-liter 3-necked flask with a mechanical stirrer and a thermocouple, keeping the reaction temperature between −15° to −5° C. The mixture is warmed to room temperature and aged for 1 h or until the reduction is complete.

Step D: Crystallization

Acetic acid (2.74 mL) is added dropwise over 10 min with rapid stirring while keeping the temperature of the mixture at 20°-25° C. This mixture is aged at room temperature for 0.5 h, followed by the addition of water (160 mL) dropwise over 1 h. The solution is seeded with imidazole 4 and followed by the addition of water (160 mL) dropwise over 1 h. The product precipitated within 0.5 h. The slurry is aged at room temperature for 2 h, cooled to 10° C., aged for 0.5 h and the solid is filtered. The cake is washed with 320 mL of water, suction dried under nitrogen at room temperature for 2 h and oven dried under house vacuum (−24 psi) at <60° C. for 12 h to afford 54.3 g of 1-bromo-4-(2'-n-butyl-4'-chloro-5'-hydroxymethylimidazole-1'H-1'-yl)methylbenzene as a white solid (HPLC assay: 98.8 A%, 97.2 W%, overall yield: 92.4%, 0.5 W% of the regioisomer).

EXAMPLE 6

2-n-Butyl-4-chloro-1-[(2'-(2-triphenylmethyl-2H-tetrazol-5-yl)-1,1'-biphenyl-4yl)methyl]-1H-imidazole-5-methanol Step A: Catalyst Preparation Triphenylphosphine (262 mg, 1.0 mmol) is dissolved in THF (20 mL) and the solution is degassed by vacuum/nitrogen purges (3×). Palladium acetate (56 mg, 0.25 mmol) is added and the solution is degassed again (3×). The resulting solution is warmed to 60° C. for 30 min. and then cooled to 25° C.

Step B: Coupling

Note: All solvents must be degassed.

2-(2'-triphenylmethyl-2'H-tetrazol-5'-yl)phenylboronic acid (15.4 g, 26.7 mmol, 75 wt % pure) is suspended in diethoxymethane (DEM) (80 mL, KF ≦500 mg/ml). Water (0.55 mL, 31 mmol) is added and the slurry is aged at ambient temperature for 30 min. After the age, another charge of water (0.55 ml, 31 mmol) is added to the boronic acid suspension under agitation. The slurry is then treated with powdered potassium carbonate (8.6 g, 62 mmol) and alkylated imidazole, the titled product of Example 6 (8.97 g, 25 mmol). The mixture is aged at 20°-25° C. for 30 min then degassed well (3×). (Note: in the pilot plant, degassing takes much longer and can be started immediately after the imidazole and carbonate are added). The catalyst solution is then charged and the mixture is heated to reflux (76°-79° C.). The reaction is complete in 2-6 hours. When the imidazole has been consumed, water (30 mL) and THF (25 ml) are added and the mixture is stirred at 55°-60° C. The water layer is separated and the organic layer is washed with water (30 mL). The organic layer is concentrated in vacuo to a volume of 50 ml to remove most of the THF. More DEM (50 ml) is added and removed by distillation to further reduce THF to≦5 vol %. The residual organic solution is diluted with warm (60° C.) DEM (to a final volume of 75 ml) and water (0.5 ml, 28 mmol). The mixture is then cooled slowly to −12° C. over 2 hours. After aging at −12° C. for 1 hour, the product is collected by filtration. The cake is washed with cold DEM (25 mL). Vacuum drying at 40° C. gave 15.5 g (93%) of the titled product (non-solvated). [Pd =600 to 1000 ppm.]

EXAMPLE 7

2-n-Butyl-4-chloro-1-[(2'-(2-triphenylmethyl-2H-tetrazol-5-yl)-1,1'-biphenyl-4-yl)methyl]-1H-imidazole-5-methanol Step A: Catalyst preparation Triphenylphosphine (262 mg, 1.0 mmol) is dissolved in THF (20 mL) and the solution is degassed by vacuum/nitrogen purges (3×). Palladium acetate (56 mg, 0.25 mmol) is added and the solution is degassed again (3×). The resulting solution is warmed to 60° C. for 30 min. and then cooled to 25° C.

Step B: Coupling

Note: All solvents must be degassed.

2-(2'-Triphenylmethyl-2'H-tetrazol-5'-yl)phenylboronic acid (15.4 g, 26.7 mmol, 75 wt % pure) is suspended in diethoxymethane (DEM) (80 mL, KF≦500 mg/ml). Water (0.55 mL, 31 mmol) is added and the slurry is aged at ambient temperature for 30 min. After the age, another charge of water (0.55 ml, 31 mmol) is added to the boronic acid suspension under agitation. The slurry is then treated with powdered potassium carbonate (8.6 g, 62 mmol) and the alkylated imidazole (8.97 g, 25 mmol). The mixture is aged at 20°-25° C. for 30 min then degassed well (3×). (Note: in the pilot plant, degassing takes much longer and can be started immediately after the imidazole and carbonate are added). The catalyst solution is then charged and the mixture is heated to reflux (76°-79° C.). The reaction is complete in 2-6 hours. When the imidazole has been consumed, water (30 mL) and THF (25 ml) are added and the mixture is stirred at 55°-60° C. The water layer is separated and the organic layer is washed with water (30 mL). Tributylphosphine (0.62 ml, 10 mol %) is added and the organic layer is concentrated in vacuo to a volume of 50 ml to remove most of the THF. More DEM (50 ml) is added and removed by distillation to further reduce THF to≦5 vol %. The residual organic solution is diluted with warm (60° C.) DEM (to a final volume of 75 ml) and water (0.5 ml, 28 mmol). The mixture is then cooled slowly to −12° C. over 2 hours. After aging at −12° C. for 1 hour, the product is collected by filtration. The cake is washed with cold DEM (25 mL). Vacuum drying at 40° C. gave 15.5 g (93%) of the titled product (non-solvated). [Pd≦10 ppm].

EXAMPLE 8

2-n-Butyl-4-chloro-1-[(2'-(2-triphenylmethyl-2H-tetrazol-5-yl)-1,1'-biphenyl-4-yl)methyl]-1H-imidazole-5-methanol as the methyl isobutyl ketone solvate A suspension of the titled product of Example 7 (5 g) in methyl isobutyl ketone (MIBK) (40 ml) is degassed (3×) and tributylphosphine (0.12 g, 8 mol %) is added. The mixture is heated to 85° C. at which time a homogeneous solution was obtained. Degassed water (0.135 g, 100 mol %) is then added and the solution is cooled to −10° C. over 2 hours. The heterogeneous solution is aged at −10° C. for 2 hours, the crystallized product is collected by filtration and washed with cold MIBK (−10° C., 15 ml). The recovery was 5.40 g of the titled product (93.9 %, as the MIBK solvate).

EXAMPLE 9

2-n-butyl-4-chloro-1-[(2'-(tetrazol-5-yl)-1,1'-biphenyl-4-yl)-methyl]-1H-imidazole-5-methanol potassium salt [Polymorph Form 1]

Step A: Deprotection

Dissolve 2.50 g of the titled product of Example 8, the methyl isobutyl ketone solvate, by adding 10 mL of 0.75M $H_2SO_4$ in 50:50MeCN:water. Age 2 hours 25 min, 23°–25° C. Add 15 mL of water in 2 min (can be added in 30 min to an hour in larger scales), and age 1.75 hours, 23°–25° C. Filter and wash with 5 mL of 20:80 MeCN:water. There was almost no starting material left in the trityl alcohol filter cake (<0.05 area%).

Step B: Free Acid Formation

Dilute the above filtrate with 13 mL of MeCN. The pH of the solution is 1.50. The temperature of the solution following neutralization and crystallization was 22°–24° C. After adding 1.5 mL of 3N NaOH (pH 1.75–1.65), the reaction is seeded with 20 mg of the free acid. Age 15 min. Slowly add the next 1 mL of 3M NaOH to allow for good crystal growth (on this scale, the addition time was 5–10 min). Age 30 min. Add the remaining 3M NaOH (pH 3.60–3.50). Age 1 hour. The white slurry is filtered and washed with 5 mL of 20:80 MeCN:water then 10 mL of water. A thorough water wash of the free acid filter cake is necessary to remove all the salts. The wash can be checked for $SO_4^{-2}$. The filter cake is dried in a vacuum oven at 35° C. for 18 hours with nitrogen purge. The yield of the free acid was 1.28 g (92.5%) and there was 54 mg (4%) of the free acid in the mother liquors.

Step C: Salt Formation

To 4.0 g (9.46 mmoles) of the free acid is added 10.9 ml of 0.842N KOH solution all in one portion. The slurry is aged at room temperature for 30 minutes, during which time most of the solid dissolves. The cloudy solution is filtered and the solids collected on a sintered glass funnel. The pH of the filtrate is measured at 9.05. The aqueous solution is added slowly to a refluxing azeotropic mixture of cyclohexane/isopropanol (69° C.) whereupon the ternary azeotrope cyclohexane/isopropanol/water (64° C.) begins to distill. When the solution is dry the temperature of the overhead rises to 69° and the potassium salt crystallizes. When the water content of the pot is <0.05% the distillation is halted and the white slurry is cooled to room temperature. Polymorph Form I, a white crystalline solid, is collected on a sintered glass funnel and washed with 10–15 ml of cyclohexane/isopropanol 67/33 and dried in a vacuum oven. (wt 3.8 g yield 95%).

EXAMPLE 10

2-n-butyl-4-chloro-1-[(2'-(tetrazol-5-yl)-1,1'-biphenyl]-1H-imidazole-5-methanol potassium salt [Polymorph Form I and Polymorph Form II]

Differential Scanning Calorimeteric Cell [DSC]

Losartan (Form I) was prepared as described in the above examples. Polymorph Form II was prepared by heating Form I in a differential scanning calorimetric (DSC) cell in an open pan to 255° C. at a heating rate of 10° C./min under a nitrogen atmosphere. The thermal properties of the polymorphs were characterized on a DSC Model 910 (Du Pont Instruments) with data analysis on a thermal analyzer Model 1090 (Du Pont Instruments).

Figure 1B:
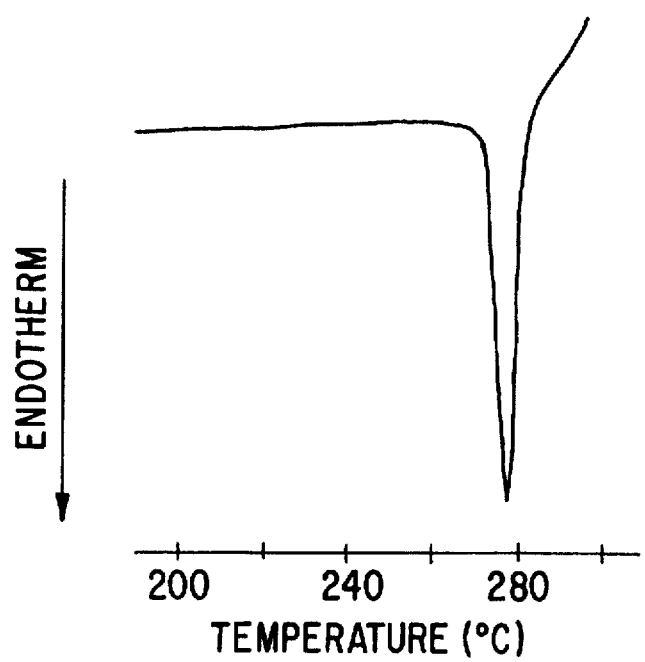

The DSC curve for Losartan (Form I) when heated at a rate of 10° C./min under a nitrogen atmosphere (FIG. 1A) shows a minor endotherm of conversion at an extrapolated onset temperature of 229.5° C. and a major melting endotherm at an extrapolated onset temperature of 273.2° C. The minor endotherm disappeared from samples which were heated to 255° C. under nitrogen at 10° C. per minute (FIG. 1B).

TABLE 1

| DSC data [samples are heated at a rate of 10°C./min under a nitrogen atmosphere(extrapolated onset temperature)] | |
|---|---|
| Form I | Form II |
| 229.5° C. (endotherm of conversion) | 273.2° C. (melting endotherm) |
| 273.2° C. (melting endotherm) | |

X-Ray Powder Diffraction [XRPD]

X-ray powder diffraction (XRPD) patterns were recorded using an automated X-ray diffractometer APD 3720 with copper tube K alpha radiation.

Figure 2A:
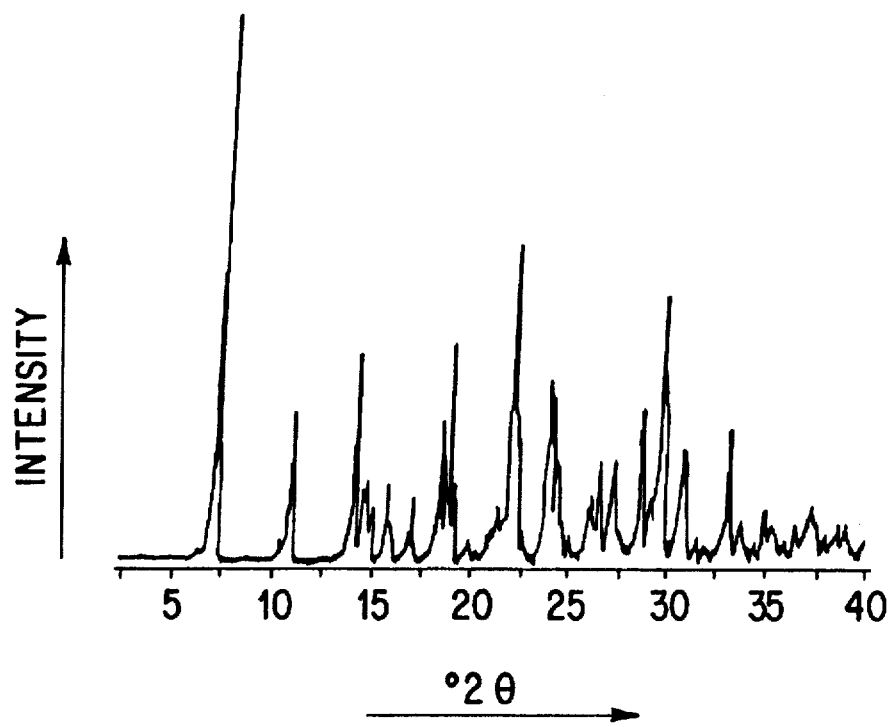
Figure 2B:
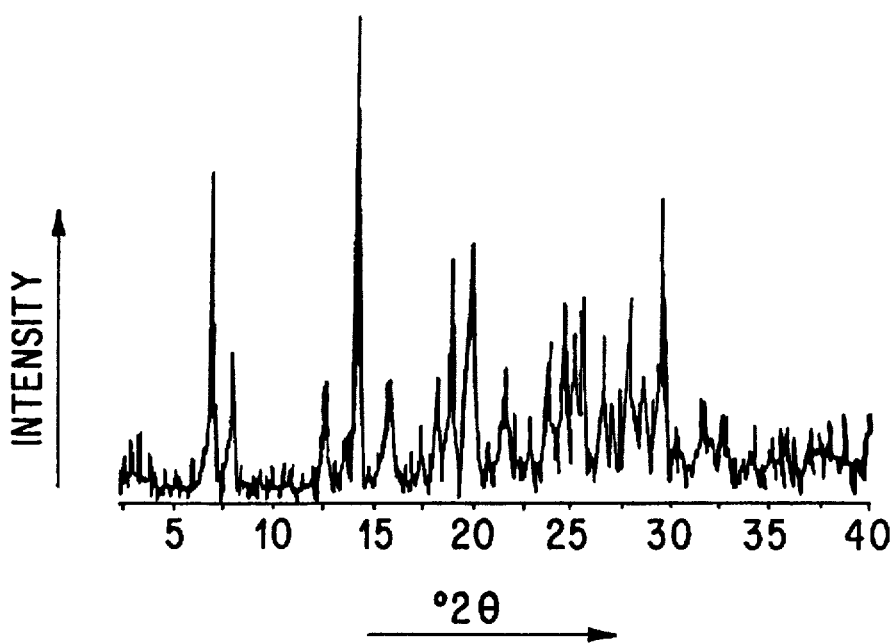

While HPLC, solution $^1$H NMR and visual inspection of the sample heated past the minor endotherm did not indicate any chemical change, the XRPD pattern (FIGS. 2A and B) indicated a change in the crystal structure. From these facts it was concluded that the minor endotherm corresponds to an enantiotropic polymorphic transition. The major endotherm is the melting of the high-temperature form. The low-temperature stable polymorph (up to the transition temperature) is designated Form I and the high-temperature stable polymorph is designated Form II. Solubility studies with Forms I and II (prepared from DSC) in nonaqueous solvents indicated that Form II converts to Form I after overnight equilibration at 25° C. in isopropanol (~35 mg/g), methyl ethyl ketone (~1 mg/g), and ethyl acetate (~0.3 mg/g). In isopropyl acetate at 25° C. after overnight equilibration, no conversion of either Form was observed and the solubilities for Forms I and II were 18 and 41 μg/mL, respectively. The solubility studies at 25° C. confirm the conclusion that Form I is the more thermodynamically stable polymorph at room temperature. Form I is the solid modification consistently obtained by solvent isolation. This was confirmed by recrystallizing the drug substance under varying conditions and analyzing by XRPD. Form II has been obtained only from DSC or related high temperature experiments.

TABLE 2

| Key diffraction angles [XRPD] | |
|---|---|
| Form I | Form II |
| 7.24 | 2.95 |
| 11.02 | 6.95 |
| 14.16 | 7.91 |
| 15.07 | 12.61 |
| 18.46 | 14.28 |
| 18.87 | 18.98 |
| 26.53 | 20.01 |
| 27.30 | 21.63 |
| 29.15 | 23.86 |
|  | 24.62 |
|  | 35.75 |

Fourier Transform Infrared Spectrum [FTIR]

Fourier transform infrared (FTIR) spectra of the two polymorphs were acquired on an Analect AQS-20 spectrometer equipped with a nitrogen-cooled MCT detector. The samples were finely ground with potassium bromide and the spectra were recorded at 4-cm$^{-1}$ resolution using a diffused reflectance accessory.

Figure 3:
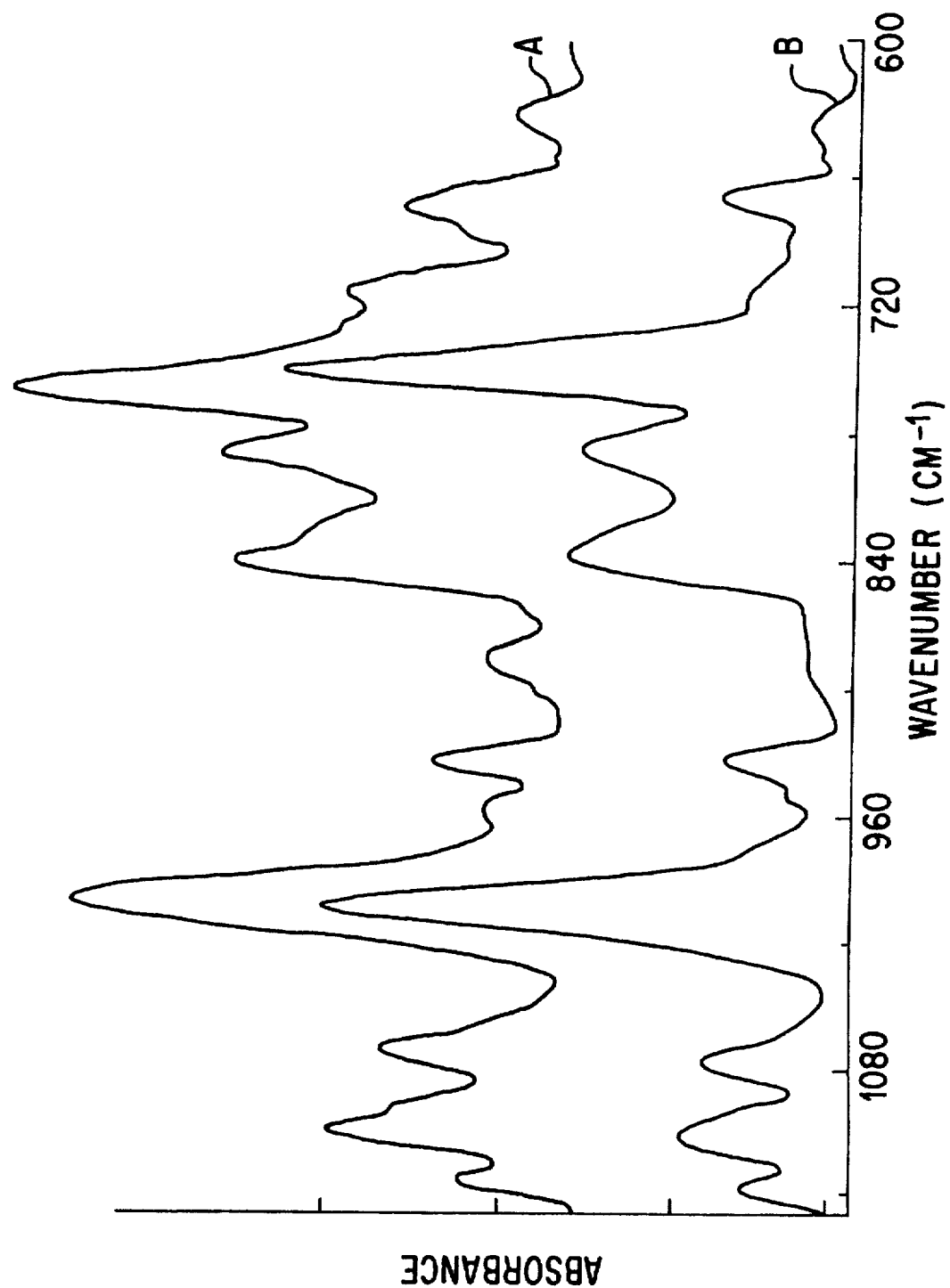
Figure 4:
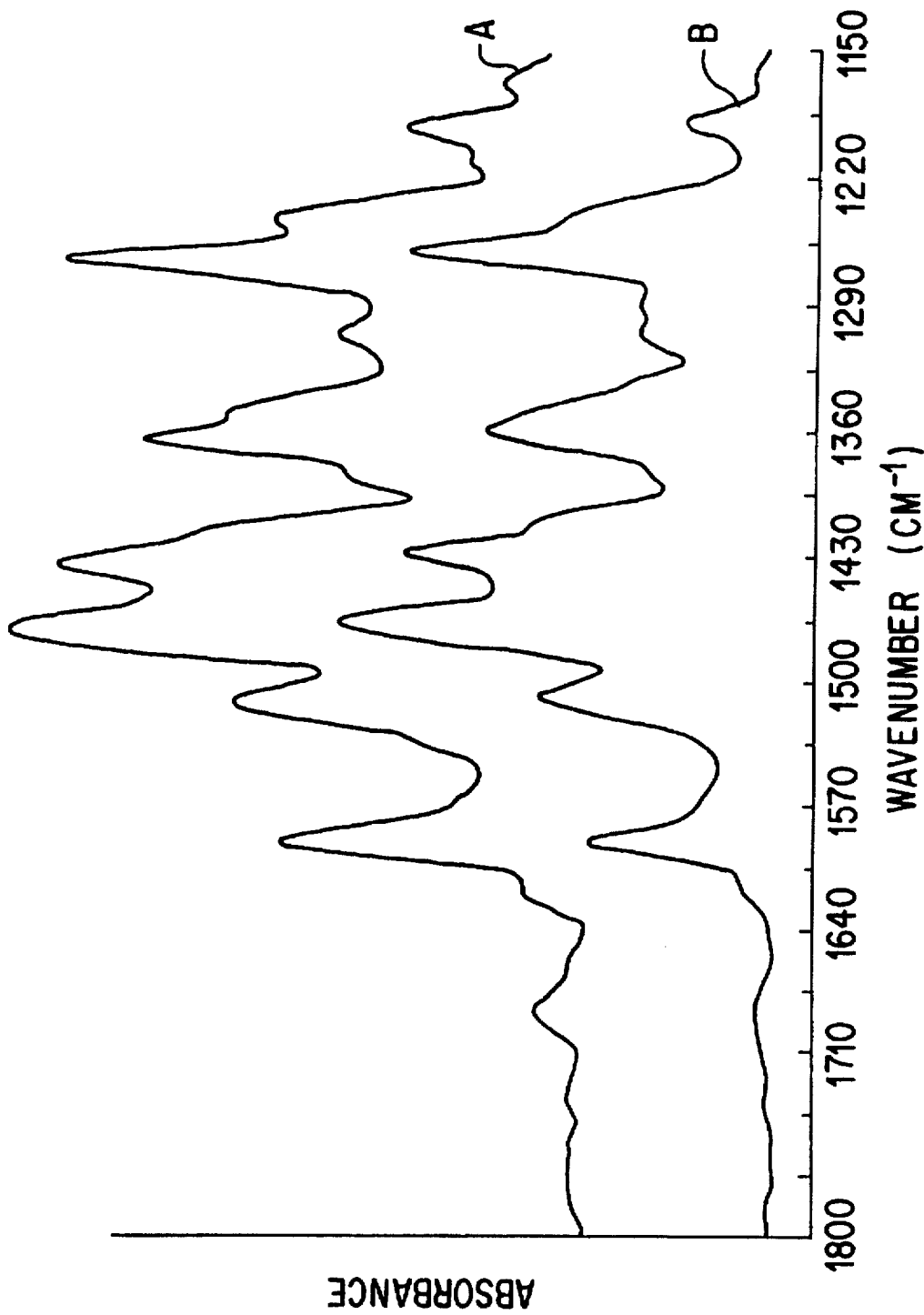

FTIR spectra of the two polymorphs in the region of 1800–600 cm$^{-1}$ are shown in FIGS. 3 and 4. While many of the spectral features are similar, there are discernible differences. Form I shows a greater multiplicity in the spectral region of 700–850 cm$^{-1}$ (FIG. 3A), where the modes are due primarily to C—H out-of-plane bending vibrations in the aromatic rings. See D. Lin-Vien, et al. In this region Form I has four modes, compared to only three modes for Form II (FIG. 3B). The additional mode in Form I arises due to splitting of the C—H out-of-plane bending mode which occurs around 750 cm$^{-1}$ in the absence of any splitting. Presumably, the molecular packing in this polymorph is such that the aromatic rings from two different molecules are so oriented allowing Van der Waals interactions and an interaction between the transition dipole moments associated with the C—H out-of-plane bending modes. Such interactions are known to cause vibrational splitting. Thus, there are two modes, at 764 and 713 cm$^{-1}$, in Form I. In Form II, the molecules are arranged differently, not allowing a similar intermolecular interaction, and only one band around 754 cm$^{-1}$ is observed. The imidazole ring modes which occur in the region of 850–970 cm$^{-1}$, See D. Lin-Vien, et al., show three absorption bands, at 886, 934, and 953 cm$^{-1}$, in Form I, compared to only one absorbance around 934 cm$^{-1}$ in Form II (FIG. 3). In the aliphatic region, a single mode around 1357 cm$^{-1}$ in Form II, attributed to the C—H symmetrical bending vibration in the methyl group of the n-butyl chain on the imidazole ring See D. Lin-Vien, et al., is observed to be split in Form I (FIG. 4). The IR data suggest that the differences in absorption pattern between the two polymorphs are due to differences in intermolecular interactions in the two crystal forms.

TABLE 3

| FTIR key spectral absorbences | |
|---|---|
| Form I | Form II |
| 764, 713 cm$^{-1}$ | 754 cm$^{-1}$ |
| 886, 934, 953 cm$^{-1}$ | 934 cm$^{-1}$ |
| 1358, 1340 cm$^{-1}$ | 1357 cm$^{-1}$ |

Raman Spectrum

Raman spectra were recorded on a Spex 1877 triple spectrometer equipped with a photomultiplier tube and optical multichannel detectors. The samples placed in quartz capillary tubes were excited by a 514.5-nm beam from a Coherent Innova-70 argon ion laser. The laser power at the samples was adjusted to about 150 mW and the spectral resolution was about 4 cm$^{-1}$.

No attempt was made to assign all the observed modes in the IR and the Raman spectra. Spectral regions where significant differences were observed for the two polymorphs were assigned based on published literature on related compounds. See D. Lin-Vien et al. *The Handbook of Infrared and Raman Characteristic Frequencies of Organic Molecules*, Academic Press, New York, 1991.

Figure 5:
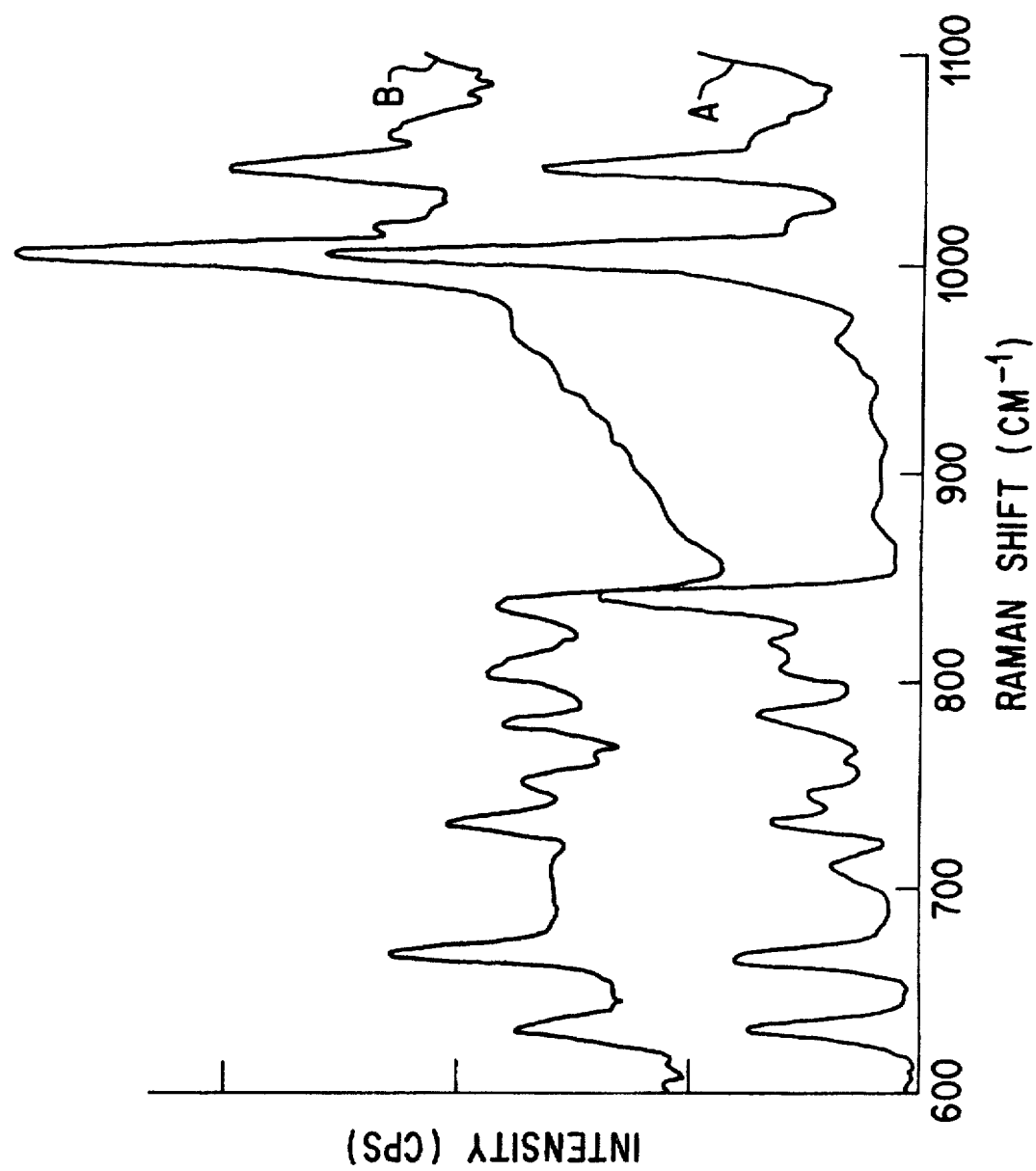

The Raman spectra of the two polymorphs in the spectral region of 600–1100 cm$^{-1}$ are shown in FIGS. 5A and B. Although Raman and infrared techniques compliment each other, they have different symmetry dependent selection rules. The C—H out-of-plane motion in the biphenyl ring, for example, is intense in the IR (around 754 cm$^{-1}$ in FIG. 3B), while it is very weak in the Raman and is observed around 763 cm$^{-1}$, See D. Lin-Vien, et al., in the Raman spectra of Form II (FIG. 5B). This band, however, is split in Form I and the two modes appear at 710 and 760 cm$^{-1}$ (FIG. 5A). A ring breathing mode associated with the imidazole ring, See D. Lin-Vien, et al., observed at 803 cm$^{-1}$ in the Raman spectra of Form II (FIG. 5B) is split in Form I, appearing at 807 and 819 cm$^{-1}$ (FIG. 5A).

Figure 6:
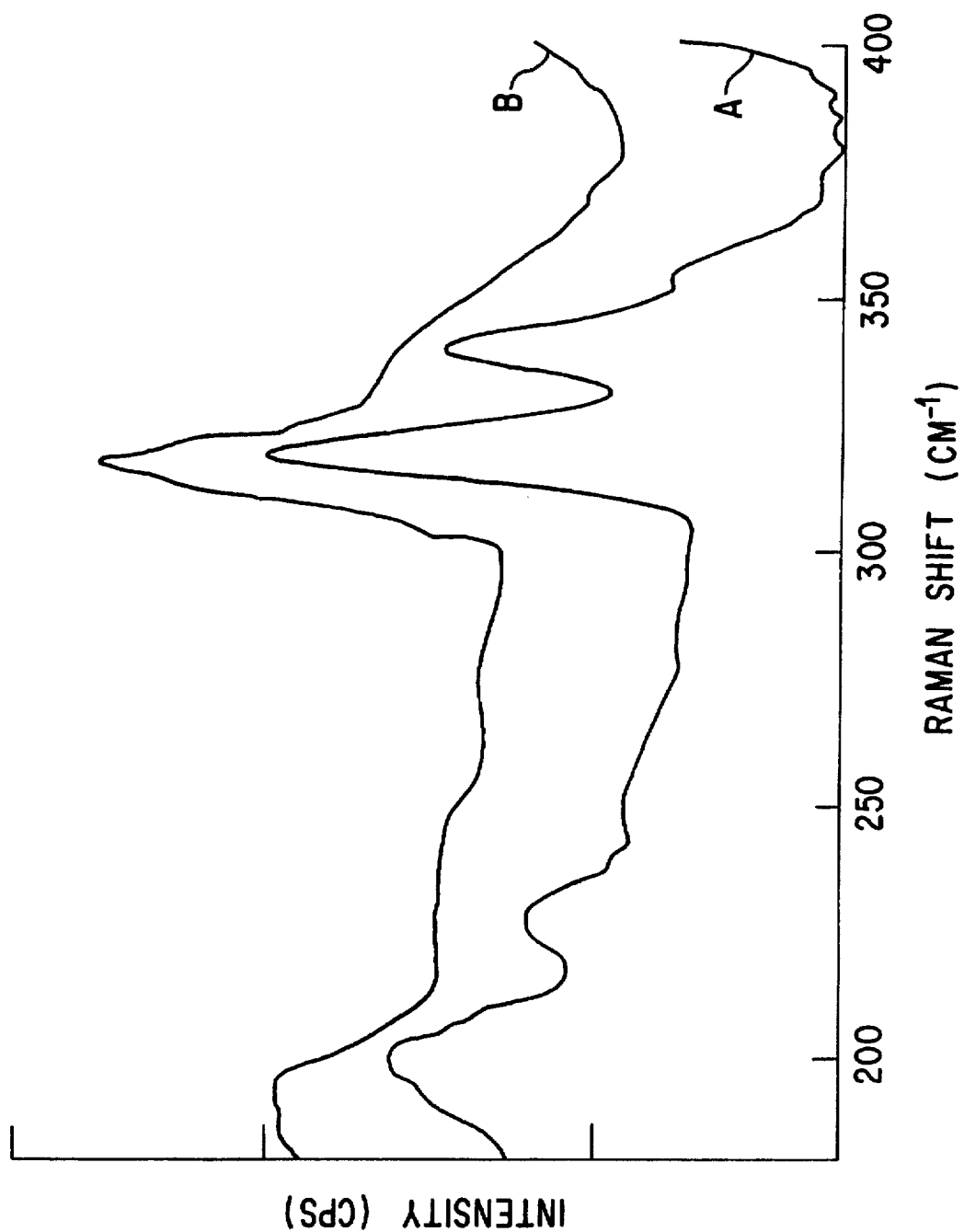

The low-frequency Raman spectroscopy provides valuable information, as the Raman modes in this region arise largely due to lattice vibrations that are very sensitive to structural changes in the solid state. See J. C. Decius, et al. The Raman modes in this region are somewhat difficult to assign because of their mixed nature. In this spectral region (FIG. 6), Form II has one band around 191 cm$^{-1}$, where there are two modes, at 199 and 227 cm$^{-1}$, in Form I. The Raman data suggest that the differences in the spectral pattern between the two polymorphs are due to differences in intermolecular interactions and differences in crystal symmetry in the two forms.

TABLE 4

| Raman key spectral modes | |
|---|---|
| Form I | Form II |
| 807, 819 cm$^{-1}$ | 803 cm$^{-1}$ |
| 710, 760 cm$^{-1}$ | 763 cm$^{-1}$ |
| 199, 227 cm$^{-1}$ | 191 cm$^{-1}$ |
| 319, 340, 354 cm$^{-1}$ | 316, 340 cm$^{-1}$ |

Solid state $^{13}$C Nuclear Magnetic Resonance Spectrum.[$^{13}$C CP/MAS NMR]

Solid-state 13C nuclear magnetic resonance spectra were acquired on a Chemagnetics CMX-360 NMR spectrometer operating at 90.5MHz for $^{13}$C and 360MHz for 1H using the CP/MAS technique. Approximately 200 mg of each polymorph was used in the acquisition of their respective spectra. All measurements were made at ambient temperature. Chemical shifts are reported on the TMS scale using hexamethylbenzene as a secondary reference. Solid-state resonance assignments were made using the interrupted decoupling pulse sequence in combination with solution-state $^{13}$C experiments performed on a GE Omega-500 high-resolution NMR spectrometer.

A positive assignment of the origin of signal multiplicities in the spectra required additional $^{13}$C CP/MAS NMR experiments to be performed at a lower static field strength. This was done on a 100-MHz spectrometer with a $^{13}$C resonance frequency of 25.2 MHz.

The solid-state $^{13}$C CP/MAS NMR spectra of the two polymorphs of Losartan are presented in FIGS. 7 (upfield region) and 8 (downfield region). Table 5 lists the chemical shifts for the two solid polymorphs of Losartan and compares them to the corresponding $^{13}$C solution-state values. Exact assignment of solid-state resonances between about 125 and 135 ppm is somewhat difficult due to the high degree of spectral overlap in this region.

The aliphatic $^{13}$C spectral region for Form I (FIG. 7A) contains more resonances than are found in the corresponding regions of Form II (FIG. 7B) or in solution (Table 5). Peaks at 14.5 and 17.2 ppm survive interrupted decoupling, implying that these are both methyl carbon signals. Since Losartan contains only one methyl group per formula unit, this suggests the presence of more than one orientation for the n-butyl side chain in the unit cell.

Figure 7A:
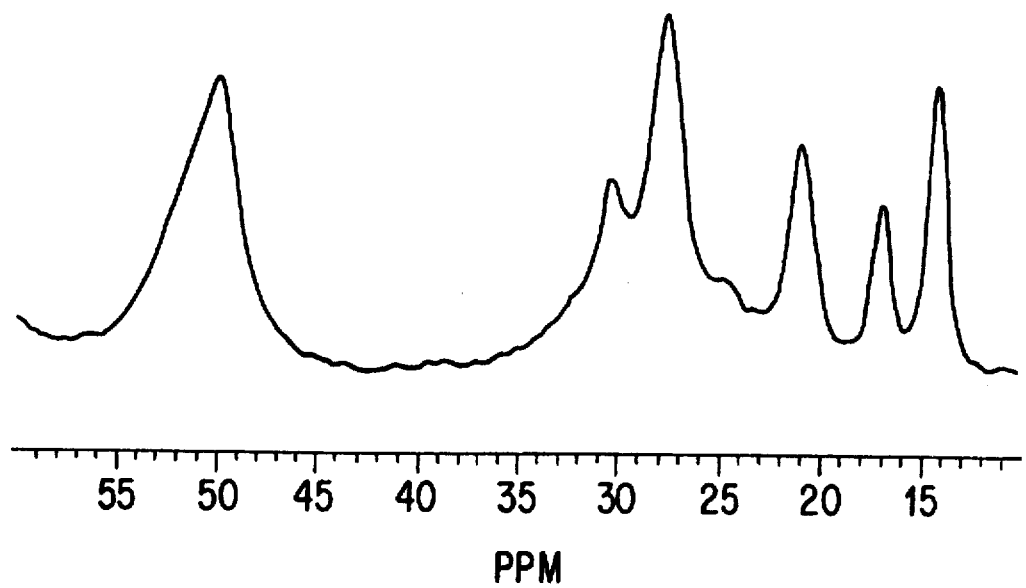

The analysis may be taken one step further by considering the relative peak areas for the two methyl signals in FIG. 7A. The observed unequal integrals of the methyl signals at 14.5 and 17.2 ppm suggest a corresponding unequal distribution of aliphatic chain conformations in the unit cell. On closer inspection, one can see similar multiplicity patterns in other resonances in FIG. 7A. Methylene carbon C8 (21.2 ppm), for example, may also account for the small signal near 25 ppm. Aliphatic signal multiplicity is actually more readily observed in the 25-MHz $^{13}$C spectrum (not shown), where it appears that at least three of the signals (C7, C8, C9) may be similarly split.

Figure 8A:
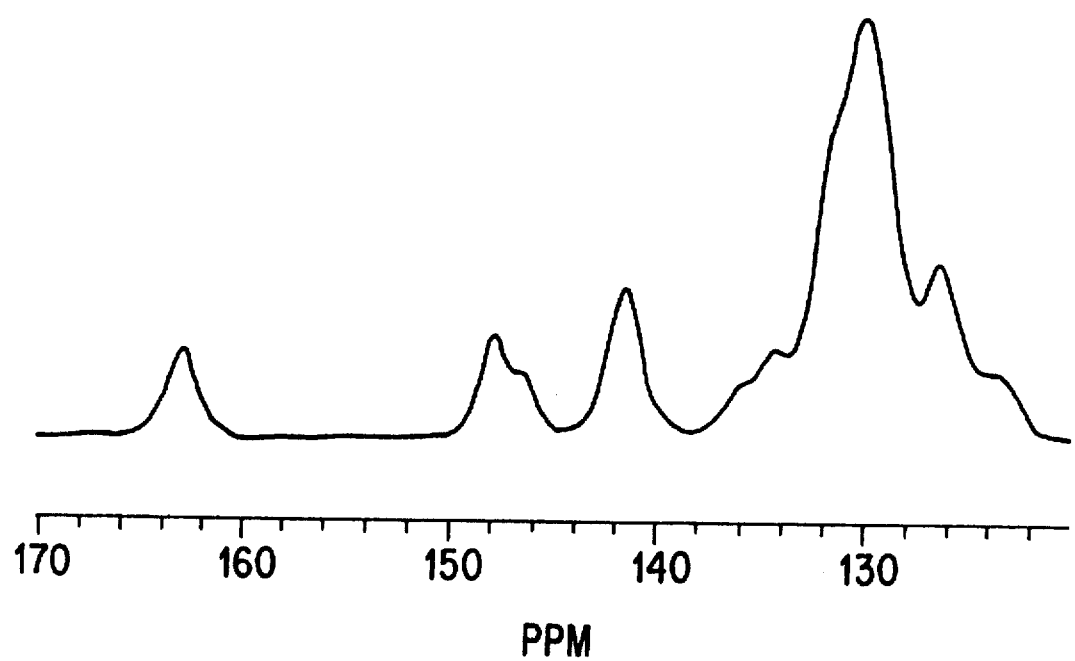

The downfield $^{13}$C spectral region of Form I is shown in FIG. 8A, and signal assignments are given in Table 5. Note that peak C2 of the imidazole ring is split into a doublet. While the pattern is rather similar to the chemical shift splitting observed for this polymorph in FIG. 7A, it is also much like that typically observed in CP/MAS spectra for $^{13}$C's attached to nitrogen. See S. J. Opella, J. G. Hexem, M. H. Frey and T. A. Cross, Solid state NMR of biopolymers, Phil. Trans. R. Soc. Lond. A 299:665–683 (1981). MAS is unable to completely remove coupling to quadrupolar nuclei like 14N, and residual broadening is often manifest as line splitting in $^{13}$C spectra. This apparent ambiguity about the origin of the C2 line shape may be sorted out by exploiting the different field dependence of the two effects [E. M. Menger and W. S. Veeman, Quadrupole effects in High-resolution phosphorus-31 solid state NMR spectra of triphenylphosphine copper (I) complexes. J. Magn. Reson. 46:257–268 (1982).] and comparing CP/MAS spectra obtained, in this case, at 90 and 25MHz. Line shapes are not consistent with residual coupling of C2 to nitrogen but, rather, indicate that the signals between 146 and 148 ppm constitute a chemical shift multiplet. The structural significance of this result then parallels that discussed for FIG. 8A above.

Figure 7B:
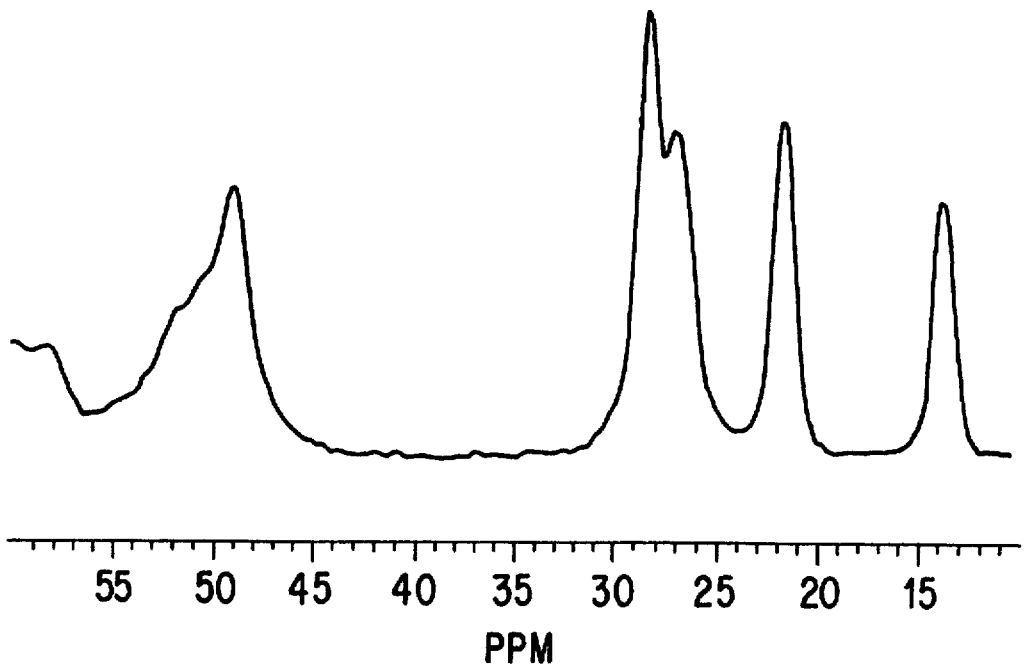
Figure 8B:
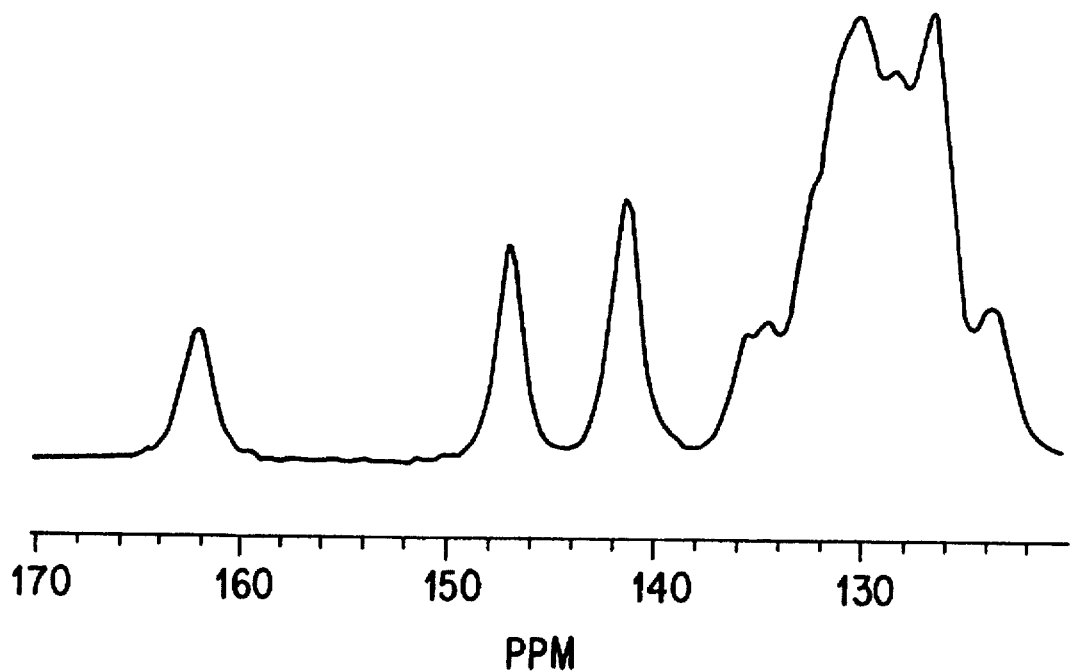

No such peak splitting is observed for the corresponding spectral regions of Form II (FIGS. 7B and 8B). Heating therefore appears to change the packing in the crystal in such a way that the unit cell of this form contains only one crystallographically unique molecule. Other, more subtle, differences, between spectra in FIGS. 7 and 8 are also indicative of packing differences between the two polymorphs under investigation. Some resonances are shifted (Table 5), and spectral intensity is clearly distributed differently in the aromatic region between about 120 and 136 ppm. It is important to note that, while heating appears to change the solid-state packing in Losartan, similar $^{13}$C line widths for the two polymorphs indicate that there is no net change in the crystallinity of the sample, concurring with the XRPD data.

A final observation regarding the high-temperature polymorph of this drug concerns dynamics of the aliphatic chain. Three of the four aliphatic resonances in FIG. 7B survive in the interrupted decoupling experiment. There is apparently enough molecular motion associated with carbons C7, C8 and C9 to render the corresponding $^{13}$C-$^{1}$H dipolar couplings weaker than those found in most rigid, crystalline solids (including Form I). This added degree of molecular motion seems consistent with a more loosely packed crystal structure for Form II.

TABLE 5

$^{13}$C chemical shifts [ppm]

| Carbon No. | Solution (DMSO-d6) | Solid State | |
|---|---|---|---|
| | | Form I | Form III |
| 21 | 160.6 | 163.2 | 162.2 |
| 2 | 147.3 | 148.1, 146.5 | 147.1 |
| 15 | 141.1 | 141.6 | 141.5 |
| 14 | 139.8 | 141.6 | 141.5 |
| 11 | 134.5 | 136.2, 134.7 | 135.6, 134.5 |
| 5 | 132.5 | 131.9 | 132.6 |
| 19 | 130.4 | 130.2 | 130.2 |
| 16 | 129.9 | 130.2 | 130.2 |
| 13, 13' | 129.3 | 130.2 | 130.2 |
| 17 | 127.2 | 130.2 | 128.4 |
| 18 | 126.6 | 130.2 | 128.4 |
| 20 | 125.5 | 126.5 | 126.7 |
| 4 | 125.3 | 123.4 | 123.6 |
| 12, 12' | 125.2 | 130.2 | 126.7 |
| CH$_2$OH | 51.3 | 50.4 | 52.0 |
| 10 | 46.5 | 50.4 | 49.1 |
| 7 | 29.0 | 30.6 | 28.3 |
| 6 | 25.8 | 27.9 | 26.8 |
| 8 | 21.6 | 21.2 | 21.5 |
| 9 | 13.6 | 17.2, 14.5 | 13.7 |

*All chemical shifts are relative to tetramethylsilane, and numbered carbon atoms refer to the numbering system presented in the above structure.

Losartan was found to exist in two enantiotropic polymorphs, a low-temperature stable Form I and a high temperature stable Form II. DSC was used along with XRPD to establish that the two forms were enantiotropically related. Solubility studies confirmed this and Form I was shown to be the most stable form at room temperature. The FTIR and Raman spectra of the two crystal forms were very similar with minor but discernible differences. The solid-state $^{13}$C NMR spectra of the two forms revealed marked differences in the chemical shift and peak splitting characteristics. The spectral characteristics of Form I were interpreted in terms of the presence of more than one orientation for the n-butyl side chain and the imidazole ring. In addition, the spectral characteristics of Form II were consistent with a large molecular motion of the n-butyl side chain at room temperature.

UTILITY

The hormone angiotensin II (AII) produces numerous biological responses (e.g. vasoconstriction) through stimulation of its receptors on cell membranes. For the purpose of identifying compounds such as AII antagonists which are capable of interacting with the AII receptor, a ligand-receptor binding assay was utilized for the initial screen. The assay was carried out according to the method described by [Glossmann, et al., *J. Biol. Chem.*, 249, 825 (1974)], but with some modifications. The reaction mixture contained rat adrenal cortical microsomes (source of AII receptor) in Tris buffer and 2 nM of $^3$H-AII with or without potential AII antagonist. This mixture was incubated for 1 hour at room temperature and the reaction was subsequently terminated by rapid filtration and rinsing through glass micro-fibre filter. Receptor-bound $^3$H-AII trapped in filter was quantitated by scintillation counting. The inhibitory concentration ($IC_{50}$) of potential AII antagonist which gives 50% displacement of the total specifically bound $^3$H-AII is presented as a measure of the affinity of such compound for the AII receptor (See Table 6).

The potential antihypertensive effects of the compounds of this invention may be demonstrated by administering the compounds to awake rats made hypertensive by ligation of the left renal artery [Cangiano, et al., *J. Pharmacol. Exp. Ther.*, 208, 310 (1979)]. This procedure increases blood pressure by increasing renin production with consequent elevation of AII levels. Compounds are administered orally at 100 mg/kg and/or intravenously via a cannula in the jugular vein at 10 mg/kg. Arterial blood pressure is continuously measured directly through a carotid artery cannula and recorded using a pressure transducer and a polygraph. Blood pressure levels after treatment are compared to pretreatment levels to determine the antihypertensive effects of the compounds (See Table 6).

TABLE 6

| Ex. No. | Angiotensin II Receptor Binding | Antihypertensive Effects in Renal Hypertensive Rats | |
|---|---|---|---|
| | $IC_{50}$ (µmolar) | Intravenous Activity[1] | Oral Activity[2] |
| Losartan | 0.039 | + | + |

[1]Significant decrease in blood pressure at 10 mg/kg or less
[2]Significant decrease in blood pressure at 100 mg/kg or less The hypotensive effects of 2-butyl-4-chloro-1-[2'-(1H-tetrazol-5-yl)biphenyl-4-yl)methyl]-5-hydroxymethylimidazole sodium salt were compared before and after furosemide administration to conscious dogs. Cumulative intravenous injections of imidazole at 0.3 to 3 mg/kg did not lower blood pressure in normotensive conscious Dogs (n=4) but they were effective in inhibiting the pressor response to AII (0.1 µg/kg iv) determined at 10 min post dose. Plasma renin activity (PRA) in these animals was 1.5±0.5 ng AI/ml/hr. Four days later, furosemide was given to three of these dogs at 10 mg/kg im at 18 and 2 hours before the experiment and increased PRA to 19.9±7.2 ng AI/ml/hr. Imidazole was then given cumulatively iv at the same doses and caused a significant decrease in blood pressure in a dose-dependent manner. It also inhibited the pressor response to AII at the two higher doses. A similar hypotensive enhancement by furosemide was also observed with captopril at 0.3 mg/kg iv. These results indicate that diuretics enhance the hypotensive efficacy of imidazole AII blockers. Thus a combined therapy of these two classes of drugs will be likely to increase the response rate to therapy among hypertensive patients.

Angiotensin II (AII) is a powerful arterial vasoconstrictor, and it exerts its action by interacting with specific receptors present on cell membranes. In order to identify AII antagonists and determine their efficacy in vitro, the following two ligand-receptor binding assays were established.

Receptor Binding Assay Using Rabbit Aortae Membrane Preparation:

Three frozen rabbit aortae (obtained from Pel-Freeze Biologicals) are suspended in 5 mM Tris-0.25M Sucrose, pH 7.4 buffer (50 ml) homogenized, and then centrifuged. The mixture is filtered through a cheesecloth and the supernatant is centrifuged for 30 minutes at 20,000 rpm at 4° C. The pellet thus obtained is resuspended in 30 ml of 50 mM Tris-5 mM $MgCl_2$ buffer containing 0.2% Bovine Serum Albumin and 0.2 mg/ml Bacitration and the suspension is used for 100 assay tubes. Samples tested for screening are done in duplicate. To the membrane preparation (0.25 ml) there is added $^{125}$I-Sar$^1$Ile$^8$-angiotensin II [obtained from New England Nuclear] (10 ul; 20,000 cpm) with or without the test sample and the mixture is incubated at 37° C. for 90 minutes. The mixture is then diluted with ice-cold 50 mM Tris-0.9% NaCl, pH 7.4 (4 ml) and filtered through a glass fiber filter (GF/B Whatman 2.4" diameter). The filter is soaked in scintillation cocktail (10 ml) and counted for radioactivity using Packard 2660 Tricarb liquid scintillation counter. The inhibitory concentration ($IC_{50}$) of a potential AII antagonist which gives 50% displacement of the total specifically bound $^{125}$I-Sar$^1$Ile$^8$-angiotensin II is presented as a measure of the efficacy of such compounds as AII antagonists.

Receptor Assay Using Bovine Adrenal Cortex Preparation

Bovine adrenal cortex is selected as the source of AII receptor. Weighed tissue (0.1 g is needed for 100 assay tubes) is suspended in Tris.HCl (50 mM), pH 7.7 buffer and homogenized. The homogenate is centrifuged at 20,000 rpm for 15 minutes. Supernatant is discarded and pellets resuspended in buffer [$Na_2HPO_4$ (10 mM)-NaCl (120 mM)-disodium EDTA (5 mM) containing phenylmethane sulfonyl fluoride (PMSF)(0.1 mM)]. (For screening of compounds, generally duplicates of tubes are used). To the membrane preparation (0.5 ml) there is added 3H-angiotensin II (50 mM)(10 µl) with or without the test sample and the mixture is incubated at 37° C. for 1 hour. The mixture is then diluted with Tris buffer (4 ml) and filtered through a glass fiber filter (GF/B Whatman 2.4" diameter). The filter is soaked in scintillation cocktail (10 ml) and counted for radioactivity using Packard 2660 Tricarb liquid scintillation counter. The inhibitory concentration ($IC_{50}$) of a potential AII antagonist which gives 50% displacement of the total specifically bound 3H-angiotensin II is presented as a measure of the efficacy of such compounds as AII antagonists.

Receptor Assay Using Rat Brain Membrane Preparation

Membranes from rat brain (thalamus, hypothalamus and midbrain) are prepared by homogenization in 50 mM Tris HCl (pH 7.4), and centrifuged at 50,000 ×g. The resulting pellets are washed twice in 100 mM NaCl, 5 mM $Na_2$.EDTA, 10 mM $Na_2HPO4$ (pH 7.4) and 0.1 mM PMSF by resuspension and centrifugation. For binding assays, the pellets are resuspended in 160 volumes of binding assay buffer (100 mM NaCl, 10 mM $Na_2HPO_4$, 5 mM $Na_2$.EDTA, pH 7.4, 0.1 mM PMSF, 0.2 mg/ml soybean trypsin inhibitor, 0.018 mg/ml o-phenanthroline, 77 mg/ml dithiothreitol and 0.14 mg/ml bacitracin. For $^{125}$I.Ile$^8$-angiotensin II binding assays, 10 µl of solvent (for total binding), Sar$^1$,Ile$^8$-angiotensin H (1 µM) (for nonspecific binding) or test compounds (for displacement) and 10 µl of [$^{125}$I]Sar$^1$,Ile$^8$-angiotensin II (23–46 pM) are added to duplicate tubes. The receptor membrane preparation (500 µl) is added to each tube to initiate the binding reaction. The reaction mixtures are incubated at 37° C. for 90 minutes. The reaction is then terminated by filtration under reduced pressure through glass-fiber GF/B filters and washed immediately 4 times with 4 ml of 5 mM ice-cold Tris HCl (pH 7.6) containing 0.15M NaCl. The radioactivity trapped on the filters is counted using a gamma counter.

Using the methodology described above, representative compounds of this invention could be evaluated and an $IC_{50}<50$ µM determined, thereby demonstrating and confirming the utility of the compounds of the invention as effective AII antagonists.

The antihypertensive effects of the compounds described in the present invention may be evaluated using the methodology described below: Male Charles River Sprague-Dawley rats (300–375 gm) are anesthetized with methohexital (Brevital; 50 mg/kg i.p.) and the trachea is cannulated with PE 205 tubing. A stainless steel pithing rod (1.5 mm thick, 150 mm long) is inserted into the orbit of the fight eye and down the spinal column. The rats are immediately placed on a Harvard Rodent Ventilator (rate—60 strokes per minute, volumn—1.1 cc per 100 grams body weight). The fight carotid artery is ligated, both left and right vagal nerves are cut, and the left carotid artery is cannulated with PE 50 tubing for drug administration, and body temperature is maintained at 37° C. by a thermostatically controlled heating pad which received input from a rectal temperature probe. Atropine (1 mg/kg i.v.) is then administered, and 15 minutes later propranolol (1 mg/kg i.v.). Thirty minutes later antagonists of formula I are administered intravenously or orally. Angiotensin II is then typically given at 5, 10, 15, 30, 45 and 60 minute intervals and every half-hour thereafter for as long as the test compound showed activity. The change in the mean arterial blood pressure is recorded for each angiotensin II challenge and the percent inhibition of the angiotensin II response is calculated.

DOSAGE FORMS

The compounds of this invention can be administered for the treatment of hypertension according to the invention by any means that effects contact of the active ingredient compound with the site of action in the body of a warm-blooded animal. For example, administration, can be parenteral, i.e., subcutaneous, intravenous, intramuscular or intra peritoneal. Alternatively, or concurrently in some cases administration can be by the oral route.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1–500 milligrams per day. Ordinarily, from 10 to 100 milligrams per day in one or more applications is effective to obtain desired results. These dosages are the effective amounts both for treatment of hypertension and for treatment of congestive heart failure, i.e., for lowering blood pressure and for correcting the hemodynamic burden on the heart to relieve the congestion.

The active ingredient can be administered orally in solid dosage forms, such as capsules, tablets, and powders, or in liquid dosage forms, such as elixirs syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

Useful pharmaceutical dosage-forms for administration of the compounds of this invention can be illustrated as follows:

CAPSULES

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

SOFT GELATIN CAPSULES

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

TABLETS

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol. The solution is made to volume with water for injection and sterilized.

SUSPENSION

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise in conjunction with another therapeutic agent. When drugs are administered in physical combination, the dosage form and administration route should be selected for compatibility with both drugs. Suitable dosages, dosage forms and administration routes are illustrated in Tables 3 and 4.

TABLE 3

Examples of NSAID's that can be combined with AII blockers of this invention:

| Drug | Dose (MG) | Formulation | Route |
|---|---|---|---|
| Indomethacin | 25 (2/3 times daily) | Tablet | Oral |
| Melcofenamate | 50–100 (2/3 times daily) | Tablet | Oral |
| Ibuprofen | 300–400 (3/4 times daily) | Tablet | Oral |
| Piroxicam | 10–20 (1/2 times daily) | Tablet | Oral |
| Sulindac | 150–200 (2 times daily) | Tablet | Oral |
| Azapropazone | 200–500 (3/4 times daily) | Tablet | Oral |

TABLE 4

Examples of diuretics that can be combined with AII blockers of this invention:

| Drug | Dose (mg) | Formulation | Route |
|---|---|---|---|
| Benzothiadizides (e.g. hydrochlorothiazide) | 5–100 (daily) | Tablet | Oral |
| Loop diuretics (e.g. furosemide) | 50–80 (daily) | Tablet | Oral |

When used with an NSAID, the dosage of AII blockers will generally be the same as when the AII blocker is used alone, i.e., 1–500 milligrams per day, ordinarily from 10 to 100 milligrams per day in one or more applications. When used with diuretics, the initial dose of AII blocker can be less, e.g., 1–100 milligrams per day and for the more active compounds 1–10 milligrams per day.

What is claimed is:

1. Form I of Losartan characterized by an endothermal maximum of conversion at an extrapolated onset temperature of 229.5° C. and an endothermal maximum of melting at an extrapolated onset temperature of 273.2° C. when heated in an open pan in a differential scanning calorimetric cell at a rate of 10° C./min under a nitrogen atmosphere and an X-ray powder diffraction pattern having X-ray powder diffraction angles: 7.24, 11.02, 14.16, 15.07, 18.46, 18.87, 26.53, 27.30, 29.15.

2. Form I of Losartan according to claim 1 further characterized by FTIR spectra from 1150 to 600 cm$^{-1}$ and 1800 to 1150 cm$^{-1}$ having spectral absorbances: 764, 713, 886, 934, 953, 1358, 1340 cm$^{-1}$.

3. Form I of Losartan according to claim 2 further characterized by solid state $^{13}$C CP/MAS NMR spectra of the upfield and downfield regions having $^{13}$C chemical shifts in parts per million as shown in the table below:

TABLE 5

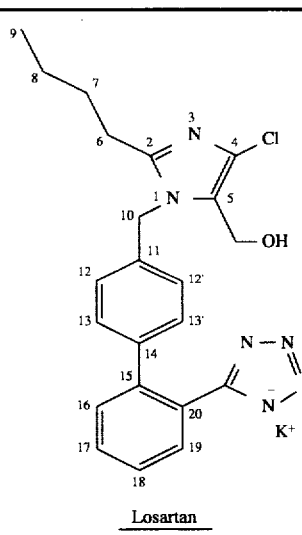

Losartan

| Carbon No. | Form 1 |
|---|---|
| 21 | 163.2 |
| 2 | 148.1, 146.5 |
| 15 | 141.6 |
| 14 | 141.6 |
| 11 | 136.2, 134.7 |
| 5 | 131.9 |
| 19 | 130.2 |
| 16 | 130.2 |
| 13, 13' | 130.2 |
| 17 | 130.2 |
| 18 | 130.2 |
| 20 | 126.5 |
| 4 | 123.4 |
| 12, 12' | 130.2 |
| CH$_2$OH | 50.4 |
| 10 | 50.4 |
| 7 | 30.6 |
| 6 | 27.9 |
| 8 | 21.2 |
| 9 | 17.2, 14.5. |

4. Form I of Losartan according to claim 3 further characterized by Raman spectra from 1100 to 600 cm$^{-1}$ and 180 to 400 cm$^{-1}$ having Raman spectral modes: 807, 819, 710, 760, 199, 227, 319, 340, 354 cm$^{-1}$.

5. Form II of Losartan characterized by an endothermal maximum of melting at an extrapolated onset temperature of 273.2° C. when heated in an open pan in a differential scanning calorimetric cell at a rate of 10° C./min under a nitrogen atmosphere and an X-ray powder diffraction pattern having X-ray powder diffraction angles: 2.95, 6.95, 7.91, 12.61, 14.28, 18.98, 20.01, 21.63, 29.15.

6. Form II of Losartan according to claim 5 further characterized by FTIR spectra from 1150 to 600 cm$^{-1}$ and 1800 to 1150 cm$^{-1}$ having spectral absorbances: 754, 934, and 1357 cm$^{-1}$.

7. Form II of Losartan according to claim 6 further characterized by solid state $^{13}$C CP/MAS NMR spectra of the upfield and downfield regions having $^{13}$C chemical shifts in parts per million as shown in the table below:

TABLE 5

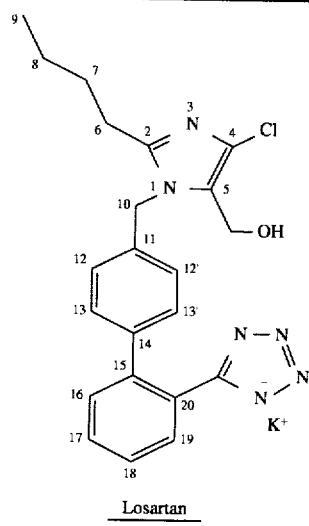

Losartan

| Carbon No. | Form II |
| --- | --- |
| 21 | 162.2 |
| 2 | 147.1 |
| 15 | 141.5 |
| 14 | 141.5 |
| 11 | 135.6, 134.5 |
| 5 | 132.6 |
| 19 | 130.2 |
| 16 | 130.2 |
| 13, 13' | 130.2 |
| 17 | 128.4 |
| 18 | 128.4 |
| 20 | 126.7 |
| 4 | 123.6 |
| 12, 12' | 126.7 |
| CH$_2$OH | 52.0 |
| 10 | 49.1 |

TABLE 5-continued

Losartan

| Carbon No. | Form II |
| --- | --- |
| 7 | 28.3 |
| 6 | 26.8 |
| 8 | 21.5 |
| 9 | 13.7. |

8. Form II of Losartan according to claim 7 further characterized by Raman spectra from 1100 to 600 cm$^{-1}$ and 180 to 400 cm$^{-1}$ having Raman spectral modes: 803, 763, 191, 316, 340 cm$^{-1}$.

9. A process for the preparation of Form II of Losartan according to claim 5 which comprises heating Form I of Losartan to a temperature range of about 230° to about 270° C. at a rate of 10° C./min.

10. The process of claim 9, wherein Form I of Losartan is heated in a differential scanning calorimetric cell in an open pan under a nitrogen atmosphere.

11. The process for the preparation of Form II of Losartan as recited in claim 10, which comprises heating Form I to a temperature of 255° C.

* * * * *

Disclaimer

5,608,075—Gordon C. Campbell, Jr., Wilmington; Anil M. Dwivedi, Newark, both of Del.; Dorothy A. Levorse, South Amboy; James A. McCauley, Bellemeade, both of N.J.; Krishnaswamy S. Raghavan, Wilmington, Del. POLYMORPHS OF LOSARTAN AND THE PROCESS FOR THE PREPARATION OF FORM II OF LOSARTAN. Patent dated March 4, 1997. Disclaimer filed by the assignees Merck & Co., Inc.; E.I. Du Pont de Nemours & Company; The DuPont Merck Pharmaceutical Company.

Hereby disclaim their entire interests in all claims (1-11).

*(Official Gazette, July 26, 2005)*

Disclaimer

5,608,075—Gordon C. Campbell, Jr., Wilmington; Anil M. Dwivedi, Newark, both of Del.; Dorothy A. Levorse, South Amboy; James A. McCauley, Bellemeade, both of N.J.; Krishnaswamy S. Raghavan, Wilmington, Del. POLYMORPHS OF LOSARTAN AND THE PROCESS FOR THE PREPARATION OF FORM II OF LOSARTAN. Patent dated March 4, 1997. Disclaimer filed by the assignees Merck & Co., Inc. May 2, 2005; E.I. Du Pont de Nemours & Company; The DuPont Merck Pharmaceutical Company.

Hereby disclaim their entire interests in all claims (1-11).

*(Official Gazette, August 30, 2005)*